(12) United States Patent
Gaddam et al.

(10) Patent No.: US 6,897,199 B2
(45) Date of Patent: May 24, 2005

(54) PHARMACEUTICALLY ACCEPTABLE SALTS OF PHENOXAZINE AND PHENOTHIAZINE COMPOUNDS

(75) Inventors: Om Reddy Gaddam, Hyderabad (IN); Ramabhadra Sarma Mamillapalli, Hyderabad (IN); Prabhakar Chebiyyam, Hyderabad (IN); Madhusudan Gutta, Hyderabad (IN)

(73) Assignee: Dr. Reddy's Laboratories Ltd., Hyderabad (IN)

(*) Notice: Subject to any disclaimer, the term of this patent is extended or adjusted under 35 U.S.C. 154(b) by 0 days.

(21) Appl. No.: 10/067,096

(22) Filed: Feb. 4, 2002

(65) Prior Publication Data

US 2002/0169146 A1 Nov. 14, 2002

Related U.S. Application Data

(60) Provisional application No. 60/267,235, filed on Feb. 5, 2001.

(51) Int. Cl.$^7$ .................... C07D 265/38; C07D 279/22; A61K 31/538; A61K 31/5415; A61P 5/48
(52) U.S. Cl. .................... 514/42; 514/226.2; 514/229.8; 536/29.1; 544/38; 544/73; 544/102
(58) Field of Search .......................... 536/29.1; 514/42, 514/226.2, 229.8; 544/38, 73, 162

(56) References Cited

U.S. PATENT DOCUMENTS

| | | | | | |
|---|---|---|---|---|---|
| 6,054,453 | A | * | 4/2000 | Lohray et al. | ........... 514/226.2 |
| 6,440,961 | B1 | * | 8/2002 | Lohray et al. | ........... 514/225.2 |

FOREIGN PATENT DOCUMENTS

| | | | |
|---|---|---|---|
| WO | WO 99/19313 A1 | * | 4/1999 |
| WO | WO 00/50414 A1 | * | 8/2000 |
| WO | 0140159 | | 6/2001 |
| WO | 0140165 | | 6/2001 |
| WO | 0140166 | | 6/2001 |
| WO | 0140169 | | 6/2001 |
| WO | 0140170 | | 6/2001 |
| WO | 0140171 | | 6/2001 |
| WO | 0140172 | | 6/2001 |
| WO | 0153257 | | 7/2001 |

OTHER PUBLICATIONS

Draetta, G. and Pagano, M. in "Annual Reports in Medicinal Chemistry, vol. 31", 1996, Academic Press, San Diego, p 241–246.*
Nuss, J.M. et al, in "Ann. Reports Med. Chem. vol. 35", 2000, Academic Press, San Diego, p 211–220.*
Cobb, J. et al, in "Ann. Reports Med. Chem. vol. 33", 1998, Academic Press, San Diego, p 213–222.*
Willson, T.M. et al, J. Med. Chem., 43 (4), 527–550, 2000.*
Par Stattin, Rudolf Kaaks. Journal of the National Cancer Institute. Oxford: Jul. 16, 2003. vol. 95, Iss. 14; p. 1086.*
Sapone, A. et al, Pharmacogenetics. Jun. 2000;10(4): 321-33, Medline 10862523.*

Ishibashi, M. et al., "Antiinflammatory and Antiarteriosclerotic Effects of Pioglitazone" Hypertension 40(5)(2002) 687–93 Abstract.
Dandona, P. "Endōthelium, inflammation, and diabetes" Curr Diab Rep 2(4) pp 311–5 (2002).
Breyer, Guan Y. "Peroxisome proliferator–activated receptors (PPARs): novel therapeutic targets in renal disease" Kidney Int. 60(1) (2001) pp 14–30 Abstract.
Dubuquoy, L., et al. "Peroxisome proliferator–activated receptor (PPAR) gamma: a new target for the treatment of inflammatory bowel disease" Gastroenterol Clin Biol 24(8–9) (2000) pp 719–24 Abstract.
Messier, Claude, et al. "Glucose regulation and cognitive functions:relation to Alzheimer's disease and diabetes" Behavioural Brain Research 75 (1996) pp 1–11.
Hull, M., et al. "Pathways of inflammatory activation in Alzheimer's disease:potential targets for disease modifying drugs" Curr Med Chem 9(1) (2002) pp 83–8 Abstract.
Watson GS, et al. "The role of insulin resistance in the pathogenesis of Alzheimer's disease: implications for treatment" CNS Drugs 17(1) (2003) pp 27–45 Abstract.
Kopelovich, L., et al. "Peroxisome proliferator–activated receptor modulators as potential chemopreventive agents" Mol Cancer Ther 1(5) (2002) pp 357–63 Abstract.
Pershadsingh, H.A. "Pharmacological peroxisome proliferator–activated receptory ligands:emerging clinical indications beyond diabetes" Expert Opin. Invest. Drugs 8(11) (1999) pp 1859–1872 Abstract.
The Diabetes–Dementia Connection, Clinician Reviews, Mar. 2000.
J. Kuusisto, et al., British Medical Journal, Association between features of the insulin resistance syndrome and Alzheimer's disease independently of apolipoprotein E4 phenotype: cross sectional population based study. No. 7115, vol. 315, Oct. 25, 1997.

(Continued)

Primary Examiner—James O. Wilson
Assistant Examiner—Thomas C. McKenzie
(74) Attorney, Agent, or Firm—Ladas & Parry LLP

(57) ABSTRACT

The present invention relates to pharmaceutically acceptable salts of compound of the general formula (I), their derivatives, their analogs, their tautomeric forms, their stereoisomers, their polymorphs, their pharmaceutically acceptable solvates and pharmaceutically acceptable compositions containing them.

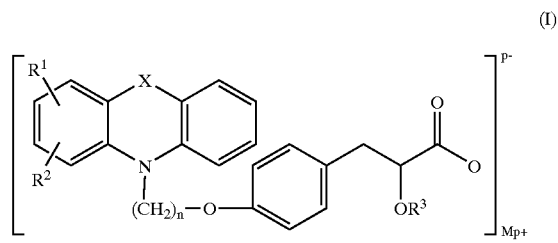

(I)

35 Claims, No Drawings

OTHER PUBLICATIONS

Gabe Mirkin, M.D., *Diabetes and Colon Cancer/Insulin Resistance*, Report #6502, May 14, 1995, CBS Radio News.

B. Isaksson, et al., *Pancreatology*, Basic: Pancreatic Cancer, 2:217–361, 2002.

Hsing AW, et al., J National Cancer Institute, *Insulin resistance and prostate cancer risk*, 95(1):67–71, Jan. 1, 2003.

Lois Baker, *University at Buffalo Reporter*, Study links cancer risk to insulin resistance, vol. 32, No. 16, Jan. 18, 2001.

Festa A, et al. Circulation, *chronic subclinical inflammation as part of the insulin resistance*, 102(1):42–7, Jul. 4, 2000.

* cited by examiner

PHARMACEUTICALLY ACCEPTABLE SALTS OF PHENOXAZINE AND PHENOTHIAZINE COMPOUNDS

This application claims the benefit of U.S. Provisional application 60/267,235 filed on Feb. 5, 2001.

FIELD OF THE INVENTION

The present invention relates to pharmaceutically acceptable salts of compound of the general formula (I), their derivatives, their analogs, their tautomeric forms, their stereoisomers, their polymorphs, their pharmaceutically acceptable solvates and pharmaceutically acceptable compositions containing them.

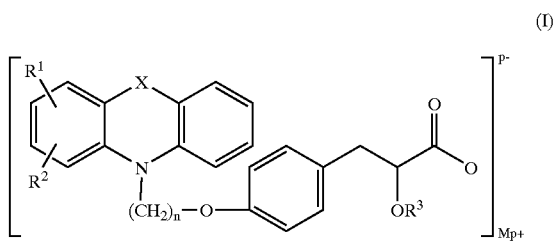

The present invention also relates to a process for the preparation of the above said pharmaceutically acceptable salts, their derivatives, their analogs, their tautomeric forms, their stereoisomers, their polymorphs, pharmaceutically acceptable solvates, and pharmaceutical compositions containing them.

The compounds of the present invention lower plasma glucose, triglycerides, lower total cholesterol (TC) and increase high density lipoprotein (HDL) and decrease low density lipoprotein (LDL), which have a beneficial effect on coronary heart disease and atherosclerosis.

The compounds of general formula (I) are useful in reducing body weight and for the treatment and/or prophylaxis of diseases such as atherosclerosis, stroke, peripheral vascular diseases and related disorders. These compounds are useful for the treatment of hyperglycemia, hyperlipidemia, hypercholesterolemia, lowering of atherogenic lipoproteins, VLDL (very low density lipoprotein) and LDL. The compounds of the present invention can be used for the treatment of certain renal diseases including glomerulonephritis, glomerulosclerosis, nephrotic syndrome, hypertensive nephrosclerosis and nephropathy. The compounds of general formula (I) are also useful for the treatment and/or prophylaxis of type 2 diabetes, leptin resistance, atherosclerosis, impaired glucose tolerance, disorders related to syndrome X such as hypertension, obesity, insulin resistance, coronary heart disease and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, eating disorders, inflammation and for the treatment of cancer. The compounds of the present invention are also useful in the treatment and/or prophylaxis of the above said diseases in combination/concomittant with one or more HMG CoA reductase inhibitors, hypolipidemic/hypolipoproteinemic agents such as fibric acid derivatives, nicotinic acid, cholestyramine, colestipol and probucol.

BACKGROUND OF INVENTION

Atherosclerosis and other peripheral vascular diseases effect the quality of life of millions of people. Therefore, considerable attention has been directed towards understanding the etiology of hypercholesterolemia and hyperlipidemia and development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as Low density lipoprotein (LDL), Intermediate density lipoprotein (IDL), High density lipoprotein (HDL) and partially as Very low density lipoprotein (VLDL). Studies clearly indicate that there is an inverse correlationship between CAD and atherosclerosis with serum HDL-cholesterol concentrations, (Stampfer et al., *N. Engl. J. Med.*, 325 (1991), 373–381) and the risk of CAD increases with increasing levels of LDL and VLDL.

In CAD, generally "fatty streaks" in carotid, coronary and cerebral arteries, are found which are primarily free and esterified cholesterol. Miller et al., (*Br. Med. J.*, 282 (1981), 1741–1744) have shown that increase in HDL-particles may decrease the number of sites of stenosis in coronary arteries of human, and high level of HDL-cholesterol may protect against the progression of atherosclerosis. Picardo et al., *Arteriosclerosis* 6 (1986) 434–441 have shown by in vitro experiment that HDL is capable of removing cholesterol from cells. They suggest that HDL may deplete tissues of excess free cholesterol and transfer it to liver (Macikinnon et al., *J. Biol. chem.* 261 (1986), 2548–2552). Therefore, agents that increase HDL cholesterol would have therapeutic significance for the treatment of hypercholesterolemia and coronary heart diseases (CHD).

Obesity is a disease highly prevalent in affluent societies and in the developing world and is a major cause of morbidity and mortality. It is a state of excess body fat accumulation. The causes of obesity are unclear. It is believed to be of genetic origin or promoted by an interaction between the genotype and environment. Irrespective of the cause, the result is fat deposition due to imbalance between the energy intake versus energy expenditure. Dieting, exercise and appetite suppression have been a part of obesity treatment. There is a need for efficient therapy to fight this disease since it may lead to coronary heart disease, diabetes, stroke, hyperlipidemia, gout, osteoarthritis, reduced fertility and many other psychological and social problems.

Diabetes and insulin resistance is yet another disease which severely effects the quality of large population in the world. Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (*J. Clin. Invest.*, 75 (1985)

809–817; N. Engl. J. Med 317 (1987) 350–357; J. Clin. Endocrinol. Metab., 66 (1988) 580–583; J. Clin. Invest., 68 (1975) 957–969) and other renal complications (patent publication No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X.

Hyperlipidemia is the primary cause for cardiovascular (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome proliferator activated receptors (PPAR) are members of the nuclear receptor super family. The gamma (γ) isoform of PPAR (PPARγ) has been implicated in regulating differentiation of adipocytes (Endocrinology, 135 (1994) 798–800) and energy homeostasis (Cell, 83 (1995) 803–812), whereas the alpha (α) isoform of PPAR (PPARα) mediates fatty acid oxidation (Trend. Endocrin. Metab., 4 (1993) 291–296) thereby resulting in reduction of circulating free fatty acid in plasma (Current Biol. 5 (1995) 618–621). PPARα agonists have been found useful for the treatment of obesity (WO 97/36579). It has been recently disclosed that there exists synergism for the molecules, which are agonists for both PPARα and PPARγ and suggested to be useful for the treatment of syndrome X (WO 97/25042). Similar synergism between the insulin sensitizer (PPARγ agonist) and HMG CoA reductase inhibitor has been observed which may be useful for the treatment of atherosclerosis and xanthoma (EP 0 753 298).

It is known that PPARγ plays an important role in adipocyte differentiation (Cell, 87 (1996) 377–389). Ligand activation of PPAR is sufficient to cause complete terminal differentiation (Cell, 79 (1994) 1147–1156) including cell cycle withdrawal. PPARγ is consistently expressed in certain cells and activation of this nuclear receptor with PPARγ agonists would stimulate the terminal differentiation of adipocyte precursors and cause morphological and molecular changes characteristics of a more differentiated, less malignant state (Molecular Cell, (1998), 465–470; Carcinogenesis, (1998), 1949–53; Proc. Natl. Acad. Sci., 94 (1997) 237–241) and inhibition of expression of prostate cancer tissue (Cancer Research 58 (1998) 3344–3352). This would be useful in the treatment of certain types of cancer, which express PPARγ and could lead to a quite nontoxic chemotherapy.

Leptin resistance is a condition wherein the target cells are unable to respond to leptin signal. This may give rise to obesity due to excess food intake and reduced energy expenditure and cause impaired glucose tolerance, type 2 diabetes, cardiovascular diseases and such other interrelated complications. Kallen et al (Proc. Natl. Acad. Sci. (1996) 93, 5793–5796) have reported that insulin sensitizers which perhaps due to the PPAR agonist expression lower plasma leptin concentrations. However, it has been recently disclosed that compounds having insulin sensitizing property also possess leptin sensitization activity. They lower the circulating plasma leptin concentrations by improving the target cell response to leptin (WO 98/02159).

In our International publication Nos. WO 99/19313 and WO 00/50414 we have disclosed and described the novel compounds of the formula (II),

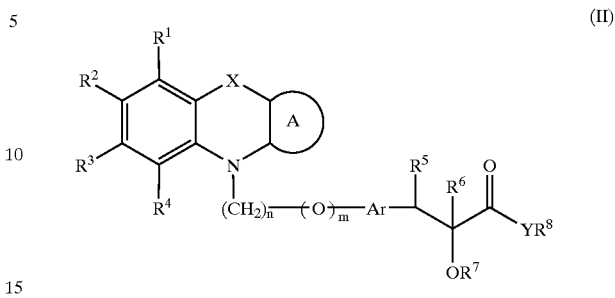

where $R^1$, $R^2$, $R^3$, $R^4$ are same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; the ring A fused to the ring containing X and N represents a 5–6 membered cyclic structure containing carbon atoms, which may optionally contain one or more heteroatoms selected from oxygen, sulfur or nitrogen atoms, which may optionally be substituted; the ring A may be saturated or contain one or more double bonds or may be aromatic; X represents a heteroatom selected from oxygen, sulfur or $NR^9$ where $R^9$ is hydrogen, alkyl, aryl, aralkyl, acyl, alkoxycarbonyl, aryloxycarbonyl or aralkoxycarbonyl; Ar represents an unsubstituted or substituted divalent single or fused aromatic or heterocyclic group; $R^5$ represents hydrogen atom, hydroxy, alkoxy, halogen, lower alkyl or unsubstituted or substituted aralkyl group or forms a bond together with the adjacent group $R^6$; $R^6$ represents hydrogen, hydroxy, alkoxy, halogen, lower alkyl group, acyl or unsubstituted or substituted aralkyl or $R^6$ forms a bond together with $R^5$; $R^7$ represents hydrogen or unsubstituted or substituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl or heteroaralkyl groups; $R^8$ represents hydrogen or unsubstituted or substituted groups selected from alkyl, cycloalkyl, aryl, aralkyl, heterocyclyl, heteroaryl or heteroaralkyl groups; Y represents oxygen or $NR^{10}$, where $R^{10}$ represents hydrogen, alkyl, aryl, hydroxyalkyl, aralkyl, heterocylcyl, heteroaryl or heteroaralkyl groups; $R^8$ and $R^{10}$ together may form a 5 or 6 membered cyclic structure containing carbon atoms, which may optionally contain one or more heteroatoms selected from oxygen, sulfur or nitrogen; n is an integer ranging from 1–4 and m is an integer 0 or 1. We have also described the processes for preparing the compounds of formula (II).

The pharmaceutically acceptable salts of the general formula (I) have significant formulation and bulk handling advantages in view of the their stability.

OBJECTS OF THE INVENTION

The present invention provides pharmaceutically acceptable salts of β-aryl-α-oxysubstituted alkylcarboxylic acids of the formula (I), their derivatives, their analogs, their tautomeric forms, their stereoisomers, their polymorphs, their pharmaceutically acceptable solvates and pharmaceutical compositions containing them or their mixtures having good stability and solubility, which can be used for the treatment and/or prophylaxis of diseases related to increased levels of lipids, especially to treat hyperlipidemia, and for the treatment of type II diabetes, impaired glucose intolerance, leptin resistance, atherosclerosis, disorders related to Syndrome X such as hypertension, obesity, insulin resistance, coronary artery disease and other cardiovascular disorders, renal diseases including glomerulonephritis, glomerulosclerosis, nephrotic syndrome, hypertensive nephrosclerosis, nephropathy; retinopathy, disorders related to endothelial cell activation, psoriasis, polycystic ovarian syndrome (PCOS), dementia, diabetic complications, eating disorders, osteoporosis, inflammatory bowel diseases, myotonic dystrophy, pancreatitis, retinopathy, arteriosclerosis, xanthoma or cancer with better efficacy, potency and lower toxicity.

The present invention provides pharmaceutically acceptable salts of β-aryl-α-oxysubstituted alkylcarboxylic acids of the formula (I) and their derivatives, their analogs, their tautomeric forms, their stereoisomers, their polymorphs, their pharmaceutically acceptable solvates and pharmaceutical compositions containing them or their mixtures which may have agonist activity against PPARα and/or PPARγ, and optionally inhibit HMG CoA reductase, in addition to agonist activity against PPARα and/or PPARγ.

The present invention provides pharmaceutically acceptable salts of β-aryl-α-oxysubstituted alkylcarboxylic acids of the formula (I) and their derivatives, their analogs, their tautomeric forms, their stereoisomers, their polymorphs, their pharmaceutically acceptable solvates and pharmaceutical compositions containing them or their mixtures having enhanced activities, without toxic effect or with reduced toxic effect.

The present invention provides a process for the preparation of pharmaceutically salts of β-aryl-α-oxysubstituted alkylcarboxylic acids and their derivatives of the formula (I) as defined above, their analogs, their tautomeric forms, their stereoisomers, their polymorphs and their pharmaceutically acceptable solvates.

The present invention provides pharmaceutical compositions containing compounds of the general formula (I), their analogs, their derivatives, their tautomers, their stereoisomers, their polymorphs, solvates or their mixtures in combination with suitable carriers, solvents, diluents and other media normally employed in preparing such compositions.

DETAILED DESCRIPTION OF THE INVENTION

The present invention relates to pharmaceutically acceptable salts having the general formula (I)

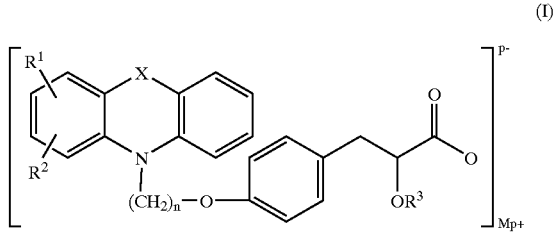

(I)

their derivatives, their analogs, their tautomeric forms, their stereoisomers, their polymorphs, wherein $R^1$ and $R^2$ may be same or different and independently represent hydrogen, halogen atom such as fluorine, chlorine, bromine or iodine; hydroxy, nitro, cyano or lower alkyl group; X represents a heteroatom selected from oxygen or sulfur; $R^3$ represents hydrogen or lower alkyl group; n is an integer ranging from 1–4; M represents a counter ion or a moiety which forms a pharmaceutically acceptable salt; p is an integer ranging from 1 to 2.

The term lower alkyl represents linear or branched $(C_1–C_6)$alkyl group, such as methyl, ethyl, n-propyl, iso-propyl, n-butyl, iso-butyl, t-butyl, n-pentyl, iso-pentyl, hexyl and the like.

Suitable groups represented by M may be selected from Li, glucamine, N-methyl glucamine, N-octyl glucamine, dicyclohexylamine, phenyl ethylamine, tris(hydroxymethyl) amino methane (tromethamine), phenyl glycinol, phenylalaninol, metformin, aminoguanidine, aminoguanidine hydrogen carbonate, imidazole, piperazine, dimethyl piperazine, pyrrolidine, benzylamine, phenyl glycine methyl ester, phenylalanine benzyl ester, t-butyl amine or morpholine.

Suitable n is an integer ranging from 1 to 4, preferably n represents an integer 1 or 2.

Particularly useful compounds according to the present invention include:

(±) 3-[4-[2-(Phenoxazin-10-yl)ethoxy]phenyl]-2-ethoxypropanoic acid imidazole salt;
(+) 3-[4-[2-(Phenoxazin-10-yl)ethoxy]phenyl]-2-ethoxypropanoic acid imidazole salt;
(−) 3-[4-[2-(Phenoxazin-10-yl)ethoxy]phenyl]-2-ethoxypropanoic acid imidazole salt;
(±) Di 3-[4-[2-(Phenoxazin-10-yl)ethoxy]phenyl]-2-ethoxypropanoic acid Piperazine salt;
(+) Di 3-[4-[2-(Phenoxazin-10-yl)ethoxy]phenyl]-2-ethoxypropanoic acid Piperazine salt;
(−) Di 3-[4-[2-(Phenoxazin-10-yl)ethoxy]phenyl]-2-ethoxypropanoic acid Piperazine salt;
(±) 3-[4-[2-(Phenoxazin-10-yl)ethoxy]phenyl]-2-ethoxypropanoic acid metformin salt;
(+) 3-[4-[2-(Phenoxazin-10-yl)ethoxy]phenyl]-2-ethoxypropanoic acid metformin salt;
(−) 3-[4-[2-(Phenoxazin-10-yl)ethoxy]phenyl]-2-ethoxypropanoic acid metformin salt;
(±) 3-[4-[2-(Phenoxazin-10-yl)ethoxy]phenyl]-2-ethoxypropanoic acid dimethylpiperazine salt;
(+) 3-[4-[2-(Phenoxazin-10-yl)ethoxy]phenyl]-2-ethoxypropanoic acid dimethylpiperazine salt;
(−) 3-[4-[2-(Phenoxazin-10-yl)ethoxy]phenyl]-2-ethoxypropanoic acid dimethylpiperazine salt;
(±) 3-[4-[2-(Phenoxazin-10-yl)ethoxy]phenyl]-2-ethoxypropanoic acid pyrrolidine salt;
(+) 3-[4-[2-(Phenoxazin-10-yl)ethoxy]phenyl]-2-ethoxypropanoic acid pyrrolidine salt;
(−) 3-[4-[2-(Phenoxazin-10-yl)ethoxy]phenyl]-2-ethoxypropanoic acid pyrrolidine salt;
(±) 3-[4-[2-(Phenoxazin-10-yl)ethoxy]phenyl]-2-ethoxypropanoic acid benzylamine salt;
(+) 3-[4-[2-(Phenoxazin-10-yl)ethoxy]phenyl]-2-ethoxypropanoic acid benzylamine salt;
(−) 3-[4-[2-(Phenoxazin-10-yl)ethoxy]phenyl]-2-ethoxypropanoic acid benzylamine salt;
(±) 3-[4-[2-(Phenoxazin-10-yl)ethoxy]phenyl]-2-ethoxypropanoic acid 1-phenyl ethyl amine salt;
(+) 3-[4-[2-(Phenoxazin-10-yl)ethoxy]phenyl]-2-ethoxypropanoic acid 1-phenyl ethyl amine salt;
(−) 3-[4-[2-(Phenoxazin-10-yl)ethoxy]phenyl]-2-ethoxypropanoic acid 1-phenyl ethyl amine salt;
(±) 3-[4-[2-(Phenoxazin-10-yl)ethoxy]phenyl]-2-ethoxypropanoic acid phenyl glycine methyl ester salt;
(+) 3-[4-[2-(Phenoxazin-10-yl)ethoxy]phenyl]-2-ethoxypropanoic acid phenyl glycine methyl ester salt;

(−) 3-[4-[2-(Phenoxazin-10-yl)ethoxy]phenyl]-2-ethoxypropanoic acid phenyl glycine methyl ester salt;
(±) 3-[4-[2-(Phenoxazin-10-yl)ethoxy]phenyl]-2-ethoxypropanoic acid phenylalanine benzyl ester salt;
(+) 3-[4-[2-(Phenoxazin-10-yl)ethoxy]phenyl]-2-ethoxypropanoic acid phenylalanine benzyl ester salt;
(−) 3-[4-[2-(Phenoxazin-10-yl) ethoxy]phenyl]-2-ethoxypropanoic acid phenylalanine benzyl ester salt;
(±) 3-[4-[2-(Phenoxazin-10-yl)ethoxy]phenyl]-2-ethoxypropanoic acid morpholine salt;
(+) 3-[4-[2-(Phenoxazin-10-yl)ethoxy]phenyl]-2-ethoxypropanoic acid morpholine salt;
(−) 3-[4-[2-(Phenoxazin-10-yl)ethoxy]phenyl]-2-ethoxypropanoic acid morpholine salt;
(±) 3-[4-[2-(Phenothiazin-10-yl)ethoxy]phenyl]-2-ethoxypropanoic acid metformin salt,
(+) 3-[4-[2-(Phenothiazin-10-yl)ethoxy]phenyl]-2-ethoxypropanoic acid metformin salt;
(−) 3-[4-[2-(Phenothiazin-10-yl)ethoxy]phenyl]-2-ethoxypropanoic acid metformin salt;
(±) 3-[4-[2-(Phenothiazin-10-yl)ethoxy]phe-nyl]-2-ethoxypropanoic acid phenylglycinol salt;
(+) 3-[4-[2-(Phenothiazin-10-yl)ethoxy]phenyl]-2-ethoxypropanoic acid phenylglycinol salt;
(−) 3-[4-[2-(Phenothiazin-10-yl)ethoxy]phenyl]-2-ethoxypropanoic acid phenylglycinol salt;
(±) 3-[4-[2-(Phenothiazin-10-yl)ethoxy]phenyl]-2-ethoxypropanoic acid 1-phenylalaninol salt;
(+) 3-[4-[2-(Phenothiazin-10-yl)ethoxy]phenyl]-2-ethoxypropanoic acid 1-phenylalaninol salt;
(−) 3-[4-[2-(Phenothiazin-10-yl)ethoxy]phenyl]-2-ethoxypropanoic acid 1-phenylalaninol salt;
(±) 3-[4-[2-(Phenothiazin-10-yl)ethoxy]phenyl]-2-ethoxypropanoic acid 1-phenyl ethylamine salt;
(+) 3-[4-[2-(Phenothiazin-10-yl)ethoxy]phenyl]-2-ethoxypropanoic acid 1-phenyl ethylamine salt;
(−) 3-[4-[2-(Phenothiazin-10-yl)ethoxy]phenyl]-2-ethoxypropanoic acid 1-phenyl ethylamine salt;
(±) 3-[4-[2-(Phenothiazin-10-yl)ethoxy]phenyl]-2-ethoxypropanoic acid imidazole salt;
(+) 3-[4-[2-(Phenothiazin-10-yl)ethoxy]phenyl]-2-ethoxypropanoic acid imidazole salt;
(−) 3-[4-[2-(Phenothiazin-10-yl)ethoxy]phenyl]-2-ethoxypropanoic acid imidazole salt;
Di (±) 3-[4-[2-(phenothiazin-10-yl)ethoxy]phenyl]-2-ethoxypropanoic acid piperazine salt;
Di (+) 3-[4-[2-(Phenothiazin-10-yl)ethoxy]phenyl]-2-ethoxypropanoic acid piperazine salt;
Di (−) 3-[4-[2-(phenothiazin-10-yl)ethoxy]phenyl]-2-ethoxypropanoic acid piperazine salt;
(±) 3-[4-[2-(Phenothiazin-10-yl)ethoxy]phenyl]-2-ethoxypropanoic acid dimethyl piperazine salt;
(+) 3-[4-[2-(Phenothiazin-10-yl)ethoxy]phenyl]-2-ethoxypropanoic acid dimethyl piperazine salt;
(−) 3-[4-[2-(Phenothiazin-10-yl)ethoxy]phenyl]-2-ethoxypropanoic acid dimethyl piperazine salt;
(±) 3-[4-[2-(Phenothiazin-10-yl)ethoxy]phenyl]-2-ethoxypropanoic acid benzylamine salt;
(+) 3-[4-[2-(Phenothiazin-10-yl)ethoxy]phenyl]-2-ethoxypropanoic acid benzylamine salt;
(−) 3-[4-[2-(Phenothiazin-10-yl)ethoxy]phenyl]-2-ethoxypropanoic acid benzylamine salt;
(±) 3-[4-[2-(Phenoxazin-10-yl)ethoxy]phenyl]-2-ethoxypropanoic acid dicyclohexylamine amine salt;
(+) 3-[4-[2-(Phenoxazin-10-yl)ethoxy]phenyl]-2-ethoxypropanoic acid dicyclohexylamine amine salt;
(−) 3-[4-[2-(Phenoxazin-10-yl)ethoxy]phenyl]-2-ethoxypropanoic acid dicyclohexylamine amine salt;
(±) 3-[4-[2-(Phenothiazin-10-yl)ethoxy]phenyl]-2-ethoxypropanoic acid dicyclohexylamine amine salt;
(+) 3-[4-[2-(Phenothiazin-10-yl)ethoxy]phenyl]-2-ethoxypropanoic acid dicyclohexylamine amine salt;
(−) 3-[4-[2-(Phenothiazin-10-yl)ethoxy]phenyl]-2-ethoxypropanoic acid dicyclohexylamine amine salt;
(±) 3-[4-[2-(Phenoxazin-10-yl)ethoxy]phenyl]-2-ethoxypropanoic acid amino guanidine salt;
(+) 3-[4-[2-(Phenoxazin-10-yl)ethoxy]phenyl]-2-ethoxypropanoic acid amino guanidine salt;
(−) 3-[4-[2-(Phenoxazin-10-yl)ethoxy]phenyl]-2-ethoxypropanoic acid amino guanidine salt;
(±) 3-[4-[2-(Phethioxazin-10-yl)ethoxy]phenyl]-2-ethoxypropanoic acid amino guanidine salt;
(+) 3-[4-[2-(Phenothiazin-10-yl)ethoxy]phenyl]-2-ethoxypropanoic acid amino guanidine salt;
(−) 3-[4-[2-(Phenothiazin-10-yl)ethoxy]phenyl]-2-ethoxypropanoic acid amino guanidine salt;
(±) 3-[4-[2-(Phenoxazin-10-yl)ethoxy]phenyl]-2-ethoxypropanoic acid t-butyl amine salt;
(+) 3-[4-[2-(Phenoxazin-10-yl)ethoxy]phenyl]-2-ethoxypropanoic acid t-butyl amine salt;
(−) 3-[4-[2-(Phenoxazin-10-yl)ethoxy]phenyl]-2-ethoxypropanoic acid t-butyl amine salt;
(±) 3-[4-[2-(Phethioxazin-10-yl)ethoxy]phenyl]-2-ethoxypropanoic acid t-butyl amine salt;
(+) 3-[4-[2-(Phenothiazin-10-yl)ethoxy]phenyl]-2-ethoxypropanoic acid t-butyl amine salt and
(−) 3-[4-[2-(Phenothiazin-10-yl)ethoxy]phenyl]-2-ethoxypropanoic acid t-butyl amine salt.

According to another feature of the present invention, there is provided a process for the preparation of pharmaceutically acceptable salts of the formula (I) which comprises, reacting compound of the formula (III)

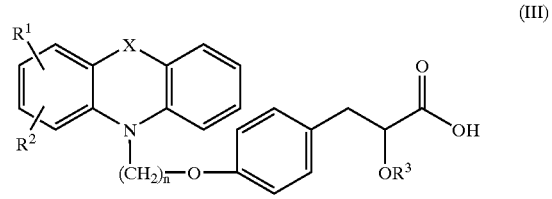

where all symbols are as defined earlier with a stoichiometric amount of an appropriate base in the presence of a solvent at a temperature in the range of −10° C. to the boiling point of the solvent employed for a period in the range of 10 minutes to 30 hours.

The compound of the formula (III) used may be either optically pure form or a racemic form. The base employed in the reaction may be selected from lithium hydroxide, glucamine, N-methyl glucamine, N-octyl glucamine, dicyclohexylamine, phenyl ethylamine, tris(hydroxymethyl) amino methane (tromethamine), phenyl glycinol, phenylalaninol, metformin, aminoguanidine, aminoguanidine hydrogen carbonate, imidazole, piperazine, dimethyl piperazine, pyrrolidine, benzylamine, phenyl glycine methyl ester, phenylalanine benzyl ester, t-butyl amine or morpholine. The solvent employed may be selected from alcohols such as ethanol, methanol, isopropanol, butanol and the like; ketones such as acetone, diethyl ketone, methyl ethyl ketone or their mixtures; ethers such as diethyl ether, ether, tetrahydrofuran, dioxane, dibutyl ether and the like or DMF, DMSO, xylene, toluene, ethyl acetate and the like or mixture thereof.

The pharmaceutically acceptable salts of the general formula (I) have significant formulation and bulk handling advantages in view of the their physicochemical properties and their stability.

Various polymorphs of a compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The stereoisomers of the compounds forming part of this invention may be prepared by using compound of formula (I) in its single enantiomeric form in the process by resolving the mixture of stereoisomers by conventional methods. Some of the preferred methods include use of microbial resolution, resolving the diastereomeric salts formed with optically pure bases such as brucine, cinchona alkaloids and their derivatives, optically pure 2-alkyl phenethyl amine, phenyl glycinol and the like. The diastereomeric salts may be obtained in pure form by fractional crystallization. Commonly used methods are compiled by Jaques et al in "Enantiomers, Racemates and Resolution" (Wiley Interscience, 1981).

Pharmaceutically acceptable solvates of the compounds of formula (I) forming part of this invention may be prepared by conventional methods such as dissolving the compounds of formula (I) in solvents such as water, methanol, ethanol and the like, preferably water and recrystallizing by using different crystallization techniques.

The present invention provides a pharmaceutical composition, containing the compounds of the general formula (I) as defined above, their derivatives, their analogs, their tautomeric forms, their stereoisomers, their polymorphs, their pharmaceutically acceptable solvates in combination with the usual pharmaceutically employed carriers, diluents and the like, useful for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglyceridemia, lowering of atherogenic lipoproteins, VLDL and LDL. The compounds of the present invention can be used for the treatment of certain renal diseases including glomerulonephritis, glomerulosclerosis, nephrotic syndrome, hypertensive nephrosclerosis, nephropathy. The compounds of general formula (I) are also useful for the treatment/prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitive functions in dementia, as inflammatory agents, treating diabetic complications, disorders related to endothelial cell activation, psoriasis, polycystic ovarian syndrome (PCOS), inflammatory bowel diseases, osteoporosis, myotonic dystrophy, pancreatitis, retinopathy, arteriosclerosis, xanthoma and for the treatment of cancer. The compounds of the present invention are useful in the treatment and/or prophylaxis of the above said diseases in combination/concomittant with one or more HMG CoA reductase inhibitors, hypolipidemic/hypolipoproteinemic agents such as fibric acid derivatives, nicotinic acid, cholestyramine, colestipol, probucol or their combination.

The compounds of the present invention in combination with HMG CoA reductase inhibitors, hypolipidemic/hypolipoproteinemic agents can be administered together or within such a period to act synergistically. The HMG CoA reductase inhibitors may be selected from those used for the treatment or prevention of hyperlipidemia such as lovastatin, pravastatin, simvastatin, fluvastatin, atorvastatin, cerivastatin and their analogs thereof. Suitable fibric acid derivative may be gemfibrozil, clofibrate, fenofibrate, ciprofibrate, benzafibrate and their analogs thereof.

The present invention also provides a pharmaceutical composition, containing the compounds of the general formula (I) as defined above, their derivatives, their analogs, their tautomeric forms, their stereoisomers, their polymorphs, their pharmaceutically acceptable solvates and one or more HMG CoA reductase inhibitors, hypolipidemic/hypolipoproteinemic agents such as fibric acid derivatives, nicotinic acid, cholestyramine, colestipol, probucol in combination with the usual pharmaceutically employed carriers, diluents and the like.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the active ingredient can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the active ingredient can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the active ingredient of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabenes.

Tablets, dragees or capsules having talc and/or a carbohydrate carried binder and the like are particularly suitable for any oral application. Preferably, carriers for tablets, dragees or capsules include lactose, corn starch and/or potato starch. A syrup or elixir can be used in cases where a sweetened vehicle can be employed.

A typical tablet production method is exemplified below:

Tablet Production Example:

| a) | | |
|---|---|---|
| | 1) Active ingredient | 30 g |
| | 2) Lactose | 95 g |
| | 3) Corn starch | 30 g |
| | 4) Carboxymethyl cellulose | 44 g |
| | 5) Magnesium stearate | 1 g |
| | | 200 g for 1000 tablets |

The ingredients 1 to 3 are uniformly blended with water and granulated after drying under reduced pressure. The ingredient 4 and 5 are mixed well with the granules and compressed by a tablet ting machine to prepare 1000 tablets each containing 30 mg of active ingredient.

| b) | | |
|---|---|---|
| | 1) Active ingredient | 30 g |
| | 2) Calcium phosphate | 90 g |
| | 3) Lactose | 40 g |
| | 4) Corn starch | 35 g |
| | 5) Polyvinyl pyrrolidone | 3.5 g |
| | 6) Magnesium stearate | 1.5 g |
| | | 200 g for 1000 tablets |

The ingredients 1–4 are uniformly moistened with an aqueous solution of 5 and granulated after drying under reduced pressure. Ingredient 6 is added and granules are compressed by a tablet ting machine to prepare 1000 tablets containing 30 mg of ingredient 1.

The compound of the formula (I) as defined above are clinically administered to mammals, including man, via either oral, nasal, pulmonary, transdermal or parenteral, rectal, depot, subcutaneous, intravenous, intraurethral, intramuscular, intranasal, ophthalmic solution or an ointment. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

The invention is explained in detail in the examples given below which are provided by way of illustration only and therefore should not be construed to limit the scope of the invention.

(−) 3-[4-[2-(Phenoxazin-10-yl)ethoxy]phenyl]-2-ethoxy propanoic acid and (−) 3-[4-[2-(phenothiazin-10-yl)ethoxy]phenyl]-2-ethoxy propanoic acid were prepared according to the procedure given in WO 99/19313 and WO 00/50414 as given below:

A solution of (−) 3-[4-[2-(phenoxazin-10-yl)ethoxy] phenyl]-2-ethoxy propanoic acid -N-(2-hydroxy-1-phenylethyl)propanamide (0.45 g, 0.84 mmol in mixture of 1M sulphuric acid (17 mL) and dioxane/water (1:1, 39 mL) was heated at 90° C. for 88 h. The pH of the mixture was adjusted to 3.0 by addition of an aqueous sodium hydrogen carbonate solution. The mixture was extracted with ethyl acetate (2×25 mL) and the organic extract was washed with water (50 mL), brine (25 mL), dried (Na$_2$SO$_4$) and evaporated. The residue was chromatographed over silica gel using a gradient of 50–75% ethyl acetate in pet. ether to afford the title compound (0.19 g, 54%) as a white solid. mp: 88–90° C.

$[\alpha]_D^{25}$=+12.6 (c=1.0%, CHCl$_3$).

However, any other procedure for preparing (−) 3-[4-[2-(phenoxazin-10-yl)ethoxy]phenyl]-2-ethoxy propanoic acid can be used. (−) 3-[4-[2-(Phenoxazin-10-yl)ethoxy]phenyl]-2-ethoxypropanoic acid, (+) 3-[4-[2-(phenoxazin-10-yl)ethoxy]phenyl]-2-ethoxypropanoic acid, (±) 3-[4-[2-(phenothiazin-10-yl)ethoxy]phenyl]-2-ethoxy propanoic acid, (+) 3-[4-[2-(phenothiazin-10-yl)ethoxy]phenyl]-2-ethoxy propanoic acid and (−) 3-[4-[2-(phenothiazin-10-yl)ethoxy]phenyl]-2-ethoxy propanoic acid can be prepared by a similar procedure described above or any procedure for making these compounds can be used.

EXAMPLE 1

(−)-3-[4-[2-(Phenoxazin-10-yl)ethoxy]phenyl]-2-ethoxypropanoic acid imidazole salt

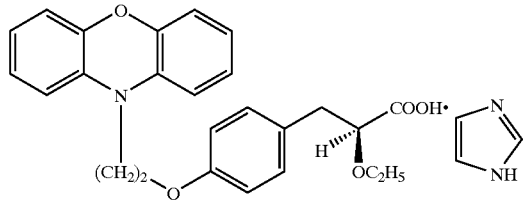

Imidazole (0.162 g, 2.38 mmol) in toluene (10 ml) was added to a solution of (−)-3-[4-[2-(phenoxazin-10-yl) ethoxy]phenyl]-2-ethoxypropanoic acid (1 g, 2.38 mmol) in toluene (5 ml). The clear reaction solution was stirred for 2 h at ambient temperature. Pet. ether (~5 ml) was added to the reaction solution, then the salt slowly precipitated and the stirring was continued for another 2 h. The precipitated product was filtered to obtain imidazole salt of (−)-3-[4-[2-(phenoxazin-10-yl)ethoxy]phenyl]-2-ethoxypropanoic acid (970 mg, yield: 83.4%; mp: 120–122° C.; chemical purity: 99.25%, chiral purity: 99.6 3% (−), 0.2% (+) by HPLC).

$^1$H NMR (200 MHz, DMSO-d$_6$): 1.0 (t, 3H), 2.8 (m, 2H), 3.2–3.6 (m, 2H), 3.9 (m, 1H), 4.0 (m, 2H), 4.2 (m, 2H), 6.6–7.2 (m, 148H), 7.7 (s, 1H)

Mass m/z: 419 (M$^+$), 420 (M$^+$+1), 210, 196, 182 and 109.

IR (KBr) cm$^{-1}$: 3432, 3061, 2925, 1590, 1491, 1272 and 1245.

EXAMPLE 2

(−)-Di 3-[4-[2-(Phenoxazin-10-yl)ethoxy]phenyl]-2-ethoxypropanoic acid Piperazine salt

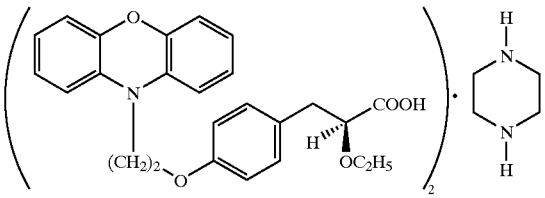

Piperazine (0.2 g, 4.77 mmol) in toluene (10 ml) was added to a solution of (−)-3-[4-[2-(phenoxazin-10-yl) ethoxy]phenyl]-2-ethoxypropanoic acid (2 g, 4.77 mmol) in toluene (5 ml). The clear reaction solution was stirred for 2 h at ambient temperature. Pet. ether (~5 ml) was added to reaction solution and the gummy mass obtained was stirred for overnight and filtered to obtain piperazine salt of (−)-3-[4-[2-(phenoxazin-10-yl)ethoxy]phenyl]-2-ethoxy propanoic acid (2.2 g, yield: 50%, mp: 77–84° C.; chemical purity: 99%; chiral purity: 99.35% (−), 0.38% (+) by HPLC).

$^1$H NMR (200 MHz, DMSO-$d_6$) shows the following signals because of two moles of S(−)-3-[4-[2-(phenoxazin-10-yl)ethoxy]phenyl]-2-ethoxypropanoic acid and one mole of piperazine. δ: 1.0 (t, 6H), 2.7 (m, 4H), 3.8 (s, 8H), 3.2–3.5 (m, 4H), 3.75, (m, 2H), 4.0 (m, 4H), 4.15 (m, 4H), 4.5 (bs, —NH), 6.6–7.2 (m, 24H).

Mass m/z: 419 (M$^+$), 420 (M$^+$+1), 210, 196, 182.

IR (KBr) cm$^{-1}$: 3464, 2872, 1586, 1490 and 1375.

EXAMPLE 3

(−)-3-[4-[2-(Phenoxazin-10-yl)ethoxy]phenyl]-2-ethoxypropanoic acid metformin salt

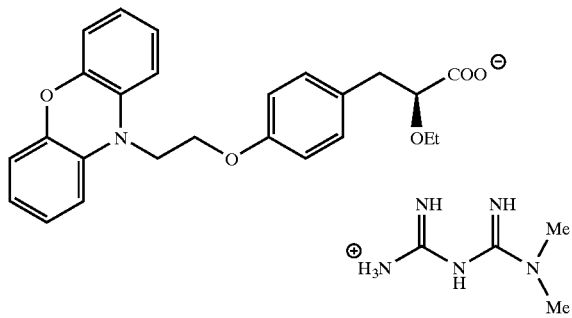

Metformin base (150 mg, 1.193 mmol) in methanol (10 ml) was added to a solution of (−)-3-[4-[2-(Phenoxazin-10-yl)ethoxy]phenyl]-2-ethoxy propanoic acid (0.5 g, 1.193 mmol.) in toluene (5 ml). The clear solution was stirred for 1 h. Methanol was distilled off and the residue was triturated with toluene (10 ml) and filtered to obtain metformin salt of (−)-3-[4-[2-(Phenoxazin-10-yl)ethoxy]phenyl]-2-ethoxy propanoic acid (370 mg, Yield: 57%, mp: 136–140° C.; Chemical HPLC 99.48%, Chiral HPLC: 97.44% (−), 2.0% (+) by HPLC)

$^1$H NMR (200 MHz) (DMSO) δ: 1.0 (m, 3H), 2.25–2.8 (m, 2H), 2.95 (s, 6H), 3.0–3.5 (m, 2H), 3.65 (m, 1H), 4.0 (m, 2H), 4.2 (m, 2H), 6.6–7.2 (m, 12H).

Mass spectrum shows m/z 419 (M$^+$) 420 (M$^+$+1), 210, 196, 182, 167, 127.

IR (KBr) shows the following absorption bands: 3426, 3335, 3105, 2923, 1654, 1566, 1488 and 1272 cm$^{-1}$.

EXAMPLE 4

(−)-3-[4-[2-(Phenoxazin-10-yl)ethoxy]phenyl]-2-ethoxypropanoic acid dimethylpiperazine salt

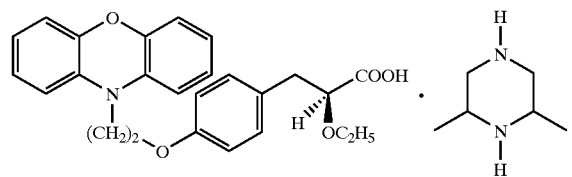

2,6-Dimethyl piperazine (0.27 g, 2.38 mmol) in toluene (10 ml) was added to a solution of (−)-3-[4-[2-(phenoxazin-10-yl)ethoxy]phenyl]-2-ethoxypropanoic acid (1 g, 2.38 mmol). The clear reaction solution was stirred for 2 h at ambient temperature. Pet. ether (~5 mg) was added to reaction solution and the gummy mass obtained was stirred for over night and filtered to obtain 2,6-dimethyl piperazine salt of (−)-3-[4-[2-(phenoxazin-10-yl)ethoxy]phenyl]-2-ethoxypropanoic acid (960 mg, yield: 75.6%, mp: 86–102° C.; chemical purity: 99.33%, chiral purity: 99.64% (−), 0.17% (+) by HPLC).

$^1$H NMR (200 MHz, DMSO-$d_6$) shows the following signals because of two moles of S(−)-3-[4-[2-(phenoxazin-10-yl)ethoxy]phenyl]-2-ethoxy propanoic acid, and one mole of piperazine,: 1.0 (m, 12H), 2.25–2.9 (m, 8H), 3.2 (q, 2H), 3.5 (q, 2H), 3.8 (m, 2H), 3.85 (m, 2H), 4.0 (m, 4H), 4.2 (m, 4H), 6.6–7.2 (m, 24H).

Mass m/z: 419 (M$^+$), 420 (M$^+$+1), 210, 196, 182, 115.

IR (KBr) cm$^{-1}$: 3439, 2925, 1512, 1492, 1376, 1274.

EXAMPLE 5

(−)-3-[4-[2-(Phenoxazin-10-yl)ethoxy]phenyl]-2-ethoxypropanoic acid pyrrolidine salt

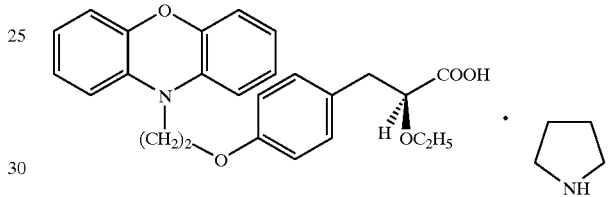

Pyrrolidine (0.17 g, 2.38 mmol) was added to the toluene (10 ml) solution of (−)-3-[4-[2-(phenoxazin-10-yl)ethoxy]phenyl]-2-ethoxypropanoic acid (1 g, 2.38 mmol). The clear reaction solution was stirred for 2 h at ambient temperature. Pet ether (~5 ml) was added to the reaction solution and the gummy mass thus obtained was stirred overnight and filtered to obtain pyrrolidine salt of (−)-3-[4-[2-(phenoxazin-10-yl) ethoxy]phenyl]-2-ethoxypropanoic acid (600 mg), yield: 68.4%, mp: 64–70° C., chemical purity: 99.4%, chiral purity: 99.8% (−), 0.18% (+) by HPLC).

$^1$H NMR (200 MHz, DMSO-$d_6$): 1.0 (t, 3H), 1.75 (s, 4H), 2.6–2.9 (m, 2H), 3.0 (s, 4H), 3.1–3.5(m, 2H), 3.6 (m, 1H), 4.0 (m, 2H), 4.2 (m, 2H), 6.6–7.1 (m, 12H)

Mass m/z: 419 (M$^+$), 420 (M$^+$+1), 210, 196, 182.

IR (KBr) cm$^{-1}$: 3429, 2920, 1590, 1490, 1375 and 1275.

EXAMPLE 6

(−)-3-[4-[2-(Phenoxazin-10-yl)ethoxy]phenyl]-2-ethoxypropanoic acid benzylamine salt

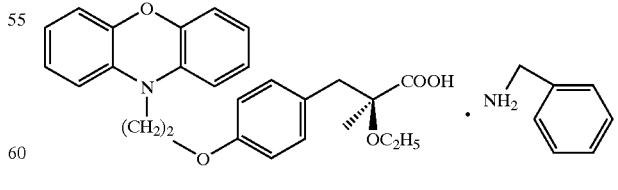

Benzylamine (0.25 g, 2.38 mmol) was added to the toluene (10 ml) solution of (−)-3-[4-[2-(phenoxazin-10-yl) ethoxy]phenyl]-2-ethoxypropanoic acid (1 g, 2.38 mol). The clear reaction solution was stirred for overnight and filtered to obtain benzylamine salt of (−)-3-[4-[2-(phenoxazin-10- yl)ethoxy]phenyl]-2-ethoxypropanoic acid (1.1 g, yield: 88%; mp: 140–144° C.; chemical purity: 99.3%, chiral purity: 99.4% (−), 0.33% (+) by HPLC).

$^1$H NMR (200 MHz, DMSO-$d_6$): 1.0 (t, 3H), 2.65–2.9 (m, 2H), 3.15 (m, 1H), 3.5 (m, 1H), 3.7 (m, 1H), 3.85 (s, 2H), 4.0 (m, 2H), 4.15 (m, 2H), 4.5 (bs, —NH$_2$), 6.6–7.45 (m, 17H)

Mass m/z: 419 (M$^+$), 420 (M$^+$+1); 210, 196, 182, 108, 91.

IR (KBr) cmn: 3427, 2871, 1552, 1511, 1491, 1376, 1274 and 1248.

EXAMPLE 7

(−)-3-[4-[2-(Phenoxazin-10-yl)ethoxy]phenyl]-2-ethoxypropanoic acid 1-phenyl ethyl amine salt

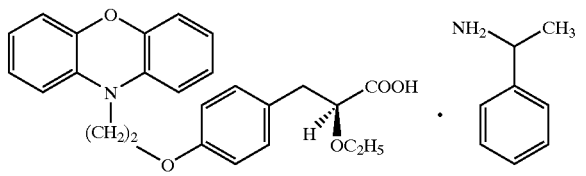

1-Phenyl ethyl amine (0.29 g, 2.38 mmol) was added to ethylacetate (20 ml) solution of (−)-3-[4-[2-(phenoxazin-10-yl)ethoxy]phenyl]-2-ethoxypropanoic acid (1 g, 2.38 mmol). The clear reaction solution was stirred for 5 h and filtered to obtain 1-phenylethyl amine salt of (−)-3-[4-[2-(phenoxazin-10-yl)ethoxy]phenyl]-2-ethoxypropanoic acid (660 mg, yield: 51.24%; mp: 113–115° C.; chemical purity 99.5%, chiral purity 99.75% (−), 0.08% (+) by HPLC).

$^1$H NMR (200 MHz, DMSO-$d_6$) δ: 1.0 (t, 3H), 1.4 (d, 3H), 2.6–2.9 (m, 2H), 3.15 (m, 1H), 3.5 (m, 1H), 3.7 (m, 1H), 4.0 (m, 2H), 4.15 (m, 2H), 4.2 (q, 1H), 6.6–7.5 (m, 17H)

Mass m/z: 419 (M$^+$), 420 (M$^+$+1), 210, 196, 182, 121 and 106.

IR (KBr) cm$^-$: 3426, 3034, 2916, 1634, 1587, 1492 and 1377.

EXAMPLE 8

(−)-3-[4-[2-(Phenoxazin-10-yl)ethoxy]phenyl]-2-ethoxypropanoic acid phenyl glycine methyl ester salt

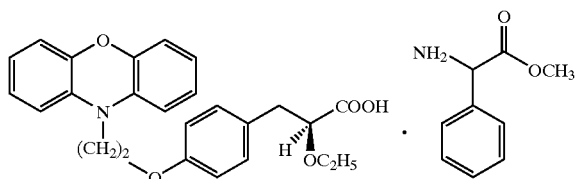

Phenyl glycine methyl ester (0.39 g, 2.38 mmol) in toluene (10 ml) was added to toluene (5 ml) solution of (−)-3-[4-[2-(phenoxazin-10-yl)ethoxy]phenyl]-2-ethoxypropanoic acid (1 g, 2.38 mmol). The clear reaction solution was stirred for 5 h and filtered to obtain phenyl glycine methyl ester salt of (−)-3-[4-[2-(phenoxazin-10-yl)ethoxy]phenyl]-2-ethoxypropanoic acid (800 mg, yield: 57.5%; mp: 113–116° C., chemical purity: 99.52%; chiral purity: 99.25% (−), 0.4% (+) by HPLC).

$^1$H NMR (200 MHz, DMSO-$d_6$) δ: 1.0 (t, 3H), 2.7–2.9 (m, 2H), 3.2–3.6 (m, 2H), 3.6 (s, 3H), 3.9 (m, 1H), 4.0 (m, 2H), 4.2 (m, 2H), 4.4 (bs, —NH$_2$), 1H), 6.6–7.4 (m, 17H).

Mass m/z: 419 (M$^+$), 420 (M$^+$+1), 210, 196, 182, 167, 106.

IR (KBr) cm$^{-1}$: 3437, 2921, 1750, 1613, 1490 and 1273.

EXAMPLE 9

(−)-3-[4-[2-(Phenoxazin-10-yl)ethoxy]phenyl]-2-ethoxypropanoic acid phenylalanine benzyl ester salt

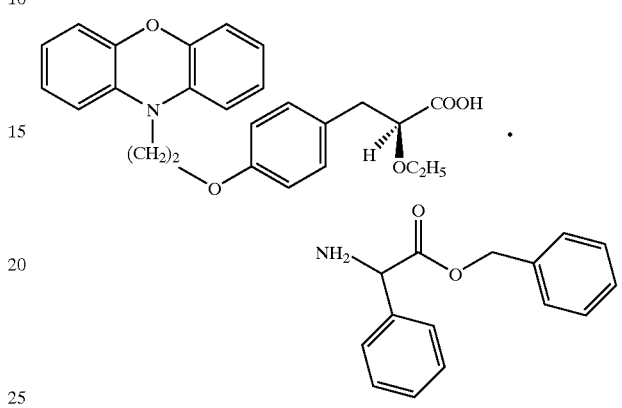

Phenylalanine benzyl ester (0.6 g, 2.38 mmol) in toluene (10 ml) was added to toluene (5 ml) solution of (−)-3-[4-[2-(phenoxazin-10-yl)ethoxy]phenyl]-2-ethoxypropanoic acid (1 g, 2.38 mmol). The clear reaction solution was stirred for 5 h at ambient temperature and filtered to obtain phenylalanine benzyl ester salt of (−)-3-[4-[2-(phenoxazin-10-yl)ethoxy]phenyl]-2-ethoxypropanoic acid (630 mg, yield: 39.37%; mp: 87–90° C.; chemical purity: 99.44%, chiral purity: 99.55% (−), 0.45% (+by HPLC).

$^1$H NMR (200 MHz, DMSO-$d_6$) δ: 1.0 (t, 3H), 2.7–2.9 (m, 2H), 2.9–3.0 (m, 2H) 3.2–3.55 (m, 2H), 3.7 (t, 1H), 3.9 (m, 1H), 4.0 (m, 2H), 4.2 (m,2H), 4.5 (bs, —NH$_2$), 5.1 (s, 2H), 2.6–7.4 (m, 22H).

Mass m/z: 419 (M$^+$), 420 (M$^+$+1), 210, 196, 182, 164, 120, 91.

IR (KBr) cm$^{-1}$: 3440, 3032, 2865, 1742, 1627, 1486, 1379 and 1272.

EXAMPLE 10

(−)-3-[4-[2-(Phenoxazin-10-yl)ethoxy]phenyl]-2-ethoxypropanoic acid morpholine salt

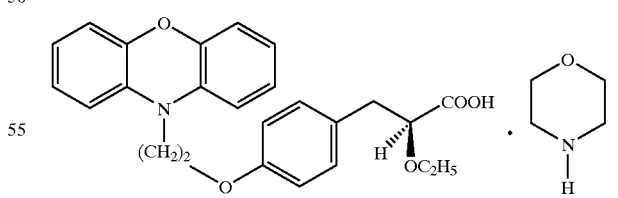

Morpholine (0.2 g, 2.3 mmol) was added to toluene (10 ml) solution of (−)-3-[4-[2-(phenoxazin-10-yl)ethoxy] phenyl]-2-ethoxypropanoic acid (1 g, 2.3 mmol.). The clear reaction solution was stirred for 3 h at ambient temperature. Pet. ether (2 ml) was added to the reaction solution and the gummy mass thus obtained was stirred overnight and filtered to obtain morpholine salt of (−)-3-[4-[2-(phenoxazin-10-yl) ethoxy]phenyl]-2-ethoxypropanoic acid (0.6 g, yield: 50%, mp: 55–62° C.; chemical purity: 98.7%, chiral purity: 99.4% (−), 0.25% (+) by HPLC).

¹H NMR (200 MHz) (DMSO-d₆): 1.0 (t, 3H), 2.75 (m, 2H), 2.8 (s, 4H), 3.2, 3.55 (m, 2H, —OCH₂—CH₃), 3.6 (s, 4H), 3.75 (m, 1H), 4.0 (m, 2H), 4.2 (m, 2H), 5.5 (bs, 1H), 6.6–7.2 (m, 12H)

Mass m/z: 419 (M⁺), 420 (M⁺+1), 210, 196, 182, 167.

IR (KBr) cm⁻¹ : 3423, 2973, 2868, 1591, 1490, 1375 and 1275.

EXAMPLE 11

(−)-3-[4-[2-(Phenoxazin-10-yl)ethoxy]phenyl]-2-ethoxypropanoic acid metformin salt

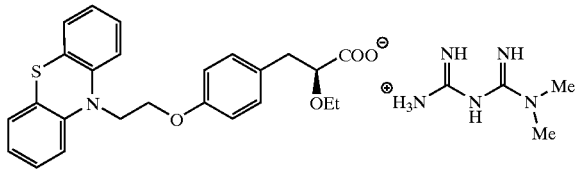

Metformin (0.29 g, 2.29 mmol) in isopropanol (5 ml) was added to the isopropanol solution of (−)-3-[4-[2-(phenothiazin-10-yl)ethoxy]phenyl]-2-ethoxypropanoic acid (1.0 g, 2.29 mmol). The clear reaction solution was stirred for four hours at ambient temperature. The isopropanol solvent was distilled off completely, added petroleum ether (20 ml) and stirred overnight to obtain gummy metformin salt of (−)-3-[4-[2-(phenothiazin-10-yl)ethoxy]phenyl]-2-ethoxypropanoic acid (1.0 g, yield: 77.5%.

¹H NMR (200 MHz, CDCl₃) δ: 1.05(t, 3H), 2.8–3.1 (m, 8H), 3.3 (q, 1H), 3.6 (q, 1H), 3.9 (m, 1H), 4.3 (m, 4H), 6.7–7.3 (m, 12H).

Mass m/z (CI method): 436 (M⁺+1), 212, 130, 113.

IR (KBr) cm⁻¹: 3438, 2965, 2361, 1612, 1570, 1462, 1239.

EXAMPLE 12

(−)-3-[4-[2-(Phenoxazin-10-yl)ethoxy]phenyl]-2-ethoxypropanoic acid phenylglycinol salt

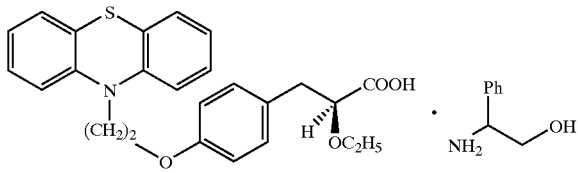

Phenylglycinol (0.31 g, 2.28 mmol) in ethylacetate (10 ml) was added to the ethylacetate (10 ml) solution of (−)-3-[4-[2-(phenothiazin-10-yl)ethoxy]phenyl]-2-ethoxypropanoic acid (1.0 g, 2.28 mmol) and the salt thus obtained was filtered to yield phenyl glycinol salt of (−)-3-[4-[2-(phenothiazin-10-yl)ethoxy]phenyl]-2-ethoxypropanoic acid (1.0 g, yield: 76.3%; mp: 160–162° C., chemical purity: 99.15%, chiral purity: 98.48%(−), 1.43%(+) by HPLC).

¹H NMR (200 MHz, CDCl₃+DMSO-d₆) δ: 1.1 (t, 3H), 2.8–3.0 (m, 2H), 3.3 (q, 1H), 3.55–3.7 (m, 3H), 3.83 (m, 1H), 4.1 (m, 1H), 4.3 (m, 4H), 5.4 (bs, —NH₂), 6.7–7.4 (m, 17H).

Mass m/z (CI method): 436 (M⁺+1), 165, 138, 121.

IR (KBr) cm⁻¹: 2871, 2643, 1612.6, 1563, 1452, 1242, 1070.

EXAMPLE 13

(−)-3-[4-[2-(Phenoxazin-10-yl)ethoxy]phenyl]-2-ethoxypropanoic acid 1-phenylalaninol salt

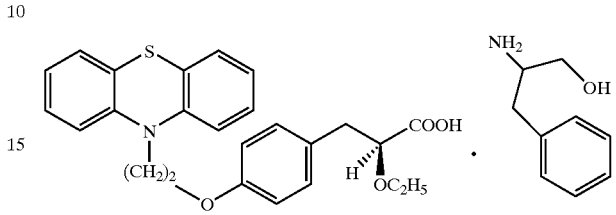

1-Phenylalaninol (0.34 g, 2.29 mmol) was added to ethylacetate (10 ml) solution of (−)-3-[4-[2-(phenothiazin-10-yl)ethoxy]phenyl]-2-ethoxypropanoic acid (1.0 g, 2.29 mmol). The clear solution was stirred for 2 h and the salt thus obtained was filtered to yield 1-phenylalaninol salt of (−)-3-[4-[2-(phenothiazin-10-yl)ethoxy]phenyl]-2-ethoxypropanoic acid (1.2 g, yield: 89.0%; mp: 88–92° C., chemical purity: 99.15%, chiral purity: 97.35%(−), 2.51% (+) by HPLC).

¹H NMR (200 MHz, CDCl₃) δ: 1.0 (t, 3H), 2.7–3.0 (m, 4H), 3.2–3.6 (m, 4H), 3.65 (m, 1H), 3.8 (m, 1H), 4.1–4.3 (m, 4H), 6.1 (bs, —NH₂), 6.7–7.3 (m, 17H).

Mass m/z (CI method): 436 (M⁺+1), 270, 152.

IR (KBr) cm⁻¹: 3991, 2883.6, 1736, 1614.5, 1550, 1450, 1238, 1113.

EXAMPLE 14

(−)-3-[4-[2-(Phenoxazin-10-yl)ethoxy]phenyl]-2-ethoxypropanoic acid 1-phenyl ethylamine salt

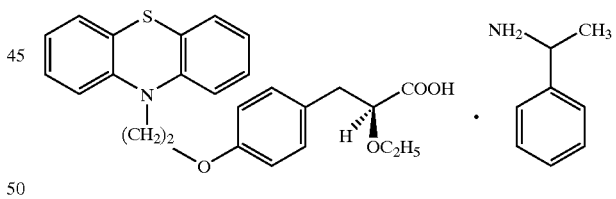

1-Phenyl ethylamine (0.27 g, 2.29 mmol) was added to toluene (20 ml) solution of (−)-3-[4-[2-(phenothiazin-10-yl)ethoxy]phenyl]-2-ethoxypropanoic acid (1.0 g, 2.29 mmol). The clear reaction solution was stirred for 2 h at ambient temperature and the salt thus obtained was filtered to yield phenyl ethylamine salt of (−)-3-[4-[2-(phenothiazin-10-yl)ethoxy]phenyl]-2-ethoxypropanoic acid (1.2 g, yield: 94.5%, mp: 140–142° C.; chemical purity: 98.12%, chiral purity: 99.69%(−), 2.95 %(+) by HPLC).

¹H NMR (200 MHz, CDCl₃) δ: 0.95 (t, 3H), 1.5 (d, 3H), 2.6–2.85 (m, 2H), 3.1 (q, 1H), 3.55 (q, 1H), 3.7 (m, 1H), 4.2 (m, 5H), 6.3 (bs, —NH₂), 6.7–7.4 (m, 17H).

Mass m/z (CI method): 436 (M⁺+1), 165, 122, 105.

IR (KBr) cm⁻¹: 2972, 2889, 2683, 1569, 1452, 1242.

EXAMPLE 15

(−)-3-[4-[2-(Phenoxazin-10-yl)ethoxy]phenyl]-2-ethoxypropanoic acid imidazole salt

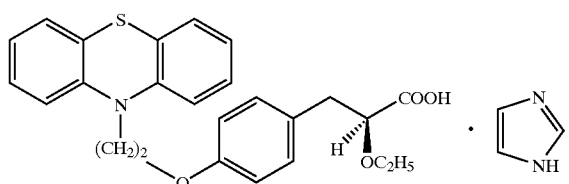

Imidazole (0.15 g, 2.29 mmol) was added to the toluene (20 ml) solution of (−)-3-[4-[2-(phenothiazin-10-yl)ethoxy]phenyl]-2-ethoxypropanoic acid 1-(1.0 g, 2.29 mmol). The clear reaction solution was stirred for 2 h at ambient temperature and the salt thus obtained was filtered to yield imidazole salt of (−)-3-[4-[2-(phenothiazin-10-yl)ethoxy]phenyl]-2-ethoxypropanoic acid (0.8 g, yield: 69.5%; mp: 170–180° C.; chemical purity: 99.0%, chiral purity: 94.12% (−), 5.6% (+) by HPLC).

$^1$H NMR (200 MHz, CDCl$_3$) δ: 1.0 (t, 3H), 2.85–3.1 (m, 2H), 3.35 (q, 1H), 3.6 (q, 1H), 4.0 (m, 1H), 4.25 (m, 4H), 6.7–7.2 (m, 14H), 8,4 (s, 1H), 9.8 (bs, 1H).

Mass m/z (CI method): 435(M$^+$), 436 (M$^+$+1), 165, 144.

IR (KBr) cm$^-$: 3415, 2979.6, 2869.3, 2477, 1569.8, 1453.3, 1240.6, 106.

EXAMPLE 16

(−)-3-[4-[2-(Phenoxazin-10-yl)ethoxy]phenyl]-2-ethoxypropanoic acid piperazine salt

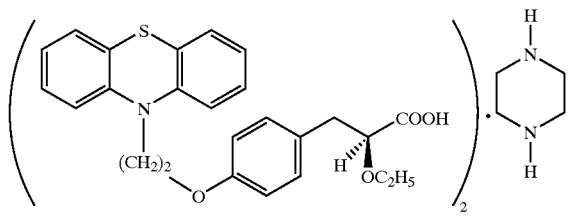

Piperazine (0.198 g, 2.29 mmol) was added to the toluene (30 ml) solution of (−)-3-[4-[2-(phenothiazin-10-yl)ethoxy]phenyl]-2-ethoxypropanoic acid (2.0 g, 4.59 mmol). The clear solution was stirred at ambient temperature for 4 h and the salt thus obtained was filtered to yield piperazine salt of di (−)-3-[4-[2-(phenothiazin-10-yl)ethoxy]phenyl]-2-ethoxypropanoic acid (2.0 g, yield: 45.5%; mp: 96–102° C.; chemical purity: 98.58%, chiral purity: 95.08%(−), 4.59% (+) by HPLC).

$^1$H NMR (200 MHz, CDCl$_3$) δ: 1.1 (t, 3H), 2.9–3.05 (m, 10H), 3.3 (q, 1H), 3.55 (q, 1H), 3.9 (m, 1H), 4.25 (m, 4H), 5.0 (bs, —NH), 6.7–7.2 (m, 12H).

Mass m/z (CI method): 435 (M$^+$), 436 (M$^+$+1), 165, 144, 108.

IR (KBr) cm$^{-1}$: 3437.7, 2965.2, 2360.8, 1612, 1570.5, 1462, 1239

EXAMPLE 17

(−)-3-[4-[2-(Phenoxazin-10-yl)ethoxy]phenyl]-2-ethoxypropanoic acid dimethyl piperazine salt

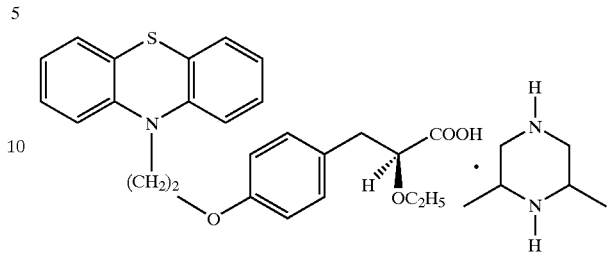

2,6-Dimethylpiperazine (0.26 g, 2.29 mmol) was added to the toluene (10 ml) solution of (−)-3-[4-[2-(phenothiazin-10-yl)ethoxy]phenyl]-2-ethoxypropanoic acid (1.0 g, 2.29 mmol). The clear reaction solution was stirred for 2 h and the salt thus obtained was filtered to yield 2,6-dimethylpiperazine salt of (−)-3-[4-[2-(phenothiazin-10-yl)ethoxy]phenyl]-2-ethoxypropanoic acid (1.0 g, yield: 79.3%; mp: 106–113° C.; chemical purity: 98.13%, chiral purity: 93.95%(−), 5.5%(+) by HPLC).

$^1$H NMR (200 MHz, CDCl$_3$) δ: 1.1 (t, 9H), 2.5–3.2 (m, 8H), 3.35 (q, 1H), 3.55 (q, 1H), 3.9 (m, 1H), 4.25 (m, 4H), 5.5 (bs, —NH), 6.7–7.2 (m, 12H)

Mass m/z (CI method): 436 (M$^+$+1), 157, 115.

IR (KBr) cm$^{-1}$: 3420.4, 2974.8, 2857, 1570.4, 1513.3, 1452, 1238.8, 1111.6.

EXAMPLE 18

(−)-3-[4-[2-(Phenoxazin-10-yl)ethoxy]phenyl]-2-ethoxypropanoic acid benzylamine salt

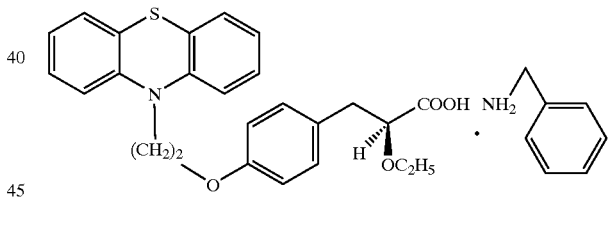

Benzylamine (0.24 g, 2.29 mmol) was added to the toluene (20 ml) solution of (−)-3-[4-[2-(phenothiazene-10-yl)ethoxy]phenyl]-2-ethoxypropanoic acid (1.0 g, 2.29 mmol). The clear reaction solution was stirred for 3 h at ambient temperature and filtered to yield benzylamine salt of 3-[4-[2-(phenothiazin-10-yl)ethoxy]phenyl]-2-ethoxypropanoic acid (1.2 g, yield: 96.8%, mp: 165–171° C., chemical purity: 98.88%, chiral purity: 96.09% (−), 3.58% (+) by HPLC).

$^1$H NMR (200 MHz, CDCl$_3$) δ: (1.0 (t, 3H), 2.65–2.9 (m, 2H), 3.1 (q, 1H), 3.4 (q, 1H), 3.75 (m, 1H), 3.8 (s, 2H), 4.2 (m, 4H), 5.8 (bs, —NH$_2$), 6.7–7.4 (m, 17H).

Mass m/z (CI method):436 (M$^+$+1), 144, 108, 91.

IR (KBr) cm$^{-1}$: 2960, 2893, 1560, 1514, 1454, 1389, 1243.

The compound of the present invention lowered random blood sugar level, triglyceride, total cholesterol, LDL, VLDL and increased HDL. This was demonstrated by in vitro as well as in vivo animal experiments.

Demonstration of Efficacy of Compounds

A) In vitro:

a) Determination of hPPARα Activity

Ligand binding domain of hPPARα was fused to DNA binding domain of Yeast transcription factor GAL4 in eucaryotic expression vector. Using superfect (Qiagen, Germany) as transfecting reagent HEK-293 cells were transfected with this plasmid and a reporter plasmid harboring the luciferase gene driven by a GAL4 specific promoter. Compound was added at different concentrations after 42 hrs of transfection and incubated overnight. Luciferase activity as a function of compound binding/activation capacity of PPARα was measured using Packard Luclite kit (Packard, USA) in Top Count (Ivan Sadowski, Brendan Bell, Peter Broag and Melvyn Hollis. Gene. 1992. 118: 137–141; Superfect Transfection Reagent Handbook. February 1997. Qiagen, Germany).

b) Determination of hPPARγ Activity

Ligand binding domain of hPPARγ1 was fused to DNA binding domain of Yeast transcription factor GAL4 in eucaryotic expression vector. Using lipofectamine (Gibco BRL, USA) as transfecting reagent HEK-293 cells were transfected with this plasmid and a reporter plasmid harboring the luciferase gene driven by a GAL4 specific promoter. Compound was added at 1 μM concentration after 48 hrs of transfection and incubated overnight. Luciferase activity as a function of drug binding/activation capacity of PPARγ1 was measured using Packard Luclite kit (Packard, USA) in Packard Top Count (Ivan Sadowski, Brendan Bell, Peter Broag and Melvyn Hollis. Gene. 1992. 118: 137–141; Guide to Eukaryotic Transfections with Cationic Lipid Reagents. Life Technologies, GIBCO BRL, USA).

| Example No. | Concentration | PPARα | Concentration | PPARγ |
|---|---|---|---|---|
| 1 | 50 μM | 4.5 | 1 μM | 11.4 |
| 2 | 50 μM | 4.0 | 1 μM | 11.2 |
| 5 | 50 μM | 4.3 | 1 μM | 11.0 |
| 7 | 50 μM | 3.43 | 1 μM | 11.45 |
| 9 | 50 μM | 4.2 | 1 μM | 10.5 |
| 12 | 50 μM | 3.7 | 1 μM | 11.84 | c) Determination of HMG CoA Reductase Inhibition Activity

Liver microsome bound reductase is prepared from 2% cholestyramine fed rats at mid-dark cycle. Spectrophotometric assays are carried out in 100 mM $KH_2PO_4$, 4 mM DTT, 0.2 mM NADPH, 0.3 mM HMG CoA and 125 μg of liver microsomal enzyme. Total reaction mixture volume is kept as 1 ml. Reaction is started by addition of HMG CoA. Reaction mixture is incubated at 37° C. for 30 min and decrease in absorbance at 340 nm is recorded. Reaction mixture without substrate is used as blank (Goldstein, J. L and Brown, M. S. Progress in understanding the LDL receptor and HMG CoA reductase, two membrane proteins that regulate the plasma cholesterol. J. Lipid Res. 1984, 25: 1450–1461). The test compounds will inhibit the HMG CoA reductase enzyme.

In vivo a) Efficacy in Genetic Models

Mutation in colonies of laboratory animals and different sensitivities to dietary regimens have made the development of animal models with non-insulin dependant diabetes and hyperlipidemia associated with obesity and insulin resistance possible. Genetic models such as db/db and ob/ob (Diabetes, (1982) 31(1): 1–6) mice and zucker fa/fa rats have been developed by the various laboratories for understanding the pathophysiology of disease and testing the efficacy of new antidiabetic compounds (Diabetes, (1983) 32: 830–838; Annu. Rep. Sankyo Res. Lab. (1994) 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, will be used in the experiment. The mice are provided with standard feed (National Institute of Nutrition (NIN), Hyderabad, India) and acidified water, ad libitum. The animals having more than 350 mg/dl blood sugar were used for testing. The number of animals in each group was 4.

Test compounds will be suspended on 0.25% carboxymethyl cellulose and administered to test group at a dose of 0.1 mg to 30 mg/kg through oral gavage daily for 6 days. The control group receives vehicle (dose 10 ml/kg). On 6th day the blood samples will be collected one hour after administration of test compounds/vehicle for assessing the biological activity.

The random blood sugar and triglyceride levels will be measured by collecting blood (100 μl) through orbital sinus, using heparinised capillary in tubes containing EDTA which was centrifuged to obtain plasma. The plasma glucose and triglyceride levels will be measured spectrometrically, by glucose oxidase and glycerol-3-$PO_4$ oxidase/peroxidase enzyme (Dr. Reddy's Lab. Diagnostic Division Kits, Hyderabad, India) methods respectively.

The blood sugar and triglycerides lowering activities of the test compound will be calculated according to the formula given below.

No adverse effects may be observed for any of the mentioned compounds of invention in the above test.

The ob/ob mice are obtained at 5 weeks of age from Bomholtgard, Denmark and are used at 8 weeks of age. Zucker fa/fa fatty rats are obtained from IffaCredo, France at 10 weeks of age and are used at 13 weeks of age. The animals are maintained under 12 hour light and dark cycle at 25+1° C. Animals are given standard laboratory chow (NIN, Hyderabad, India) and water, ad libitum (Fujiwara, T., Yoshioka, S., Yoshioka, T., Ushiyama, I and Horikoshi, H. Characterization of new oral antidiabetic agent CS-045. Studies in KK and ob/ob mice and Zucker fatty rats. Diabetes. 1988. 37: 1549–1558).

The test compounds will be administered at 0.1 to 30 mg/kg/day dose for 9 days. The control animals receives the vehicle (0.25% carboxymethylcellulose, dose 10 ml/kg) through oral gavage.

The blood samples can be collected in fed state 1 hour after drug administration on 0 and 9 day of treatment. The blood can be collected from the retro-orbital sinus through heparinised capillary in EDTA containing tubes. After centrifugation, plasma sample will be separated for triglyceride, glucose, free fatty acid, total cholesterol and insulin estimations. Measurement of plasma triglyceride, glucose, total cholesterol can be done using commercial kits (Dr. Reddy's Laboratory, Diagnostic Division, India). The plasma free fatty acid will be measured using a commercial kit from Boehringer Mannheim, Germany. The plasma insulin can be measured using a RIA kit (BARC, India). The reduction of various parameters examined will be calculated according to the formula given below.

In ob/ob mice oral glucose tolerance test is performed after 9 days treatment. Mice are fasted for 5 hrs and challenged with 3 gm/kg of glucose orally. The blood samples will be collected at 0, 15, 30, 60 and 120 min for estimation of plasma glucose levels.

b) Plasma triglyceride and Cholesterol Lowering Activity in Hypercholesterolemic Rat Models Male Sprague Dawley rats (NIN stock) were bred in DRF animal house. Animals were maintained under 12 hour light and dark cycle at 25±1° C. Rats of 180–200 gram body weight range were used for the experiment. Animals are made hypercholesterolemic by feeding 2% cholesterol and 1% sodium cholate mixed with standard laboratory chow [National Institute of Nutrition (NIN), Hyderabad, India] for 6 days. Throughout the experimental period the animals are maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988.74: 215–225).

The test compounds were administered orally at a dose 0.1 to 30 mg/kg/day for 3 days. Control group is treated with vehicle alone (0.25% Carboxymethylcellulose; dose 10 ml/kg).

The blood samples were collected in fed state 1 hour after drug administration on 0 and 3 day of compound treatment. The blood was collected from the retro-orbital sinus through heparinised capillary in EDTA containing tubes. After centrifugation, plasma sample is separated for total cholesterol, HDL and triglyceride estimations. Measurement of plasma triglyceride (TG), total cholesterol (TC) and HDL are done using commercial kits (Dr. Reddy's Laboratory, Diagnostic Division, India). LDL and VLDL cholesterol were calculated from the data obtained for total cholesterol, HDL and triglyceride. The reduction of various parameters examined are calculated according to the formula given below.

| Example No. | Dose (mg/kg) | TG | TC | HDL | LDL | VLDL |
|---|---|---|---|---|---|---|
| 3 | 10 | 47 | 82 | 64 | 46 | 82 | c) Plasma triglyceride and total cholesterol lowering activity in Swiss albino mice and Guinea pigs Male Swiss albino mice (SAM) and make Guinea pigs are obtained from NIN and housed in DRF animal house. All these animals are maintained under 12 hour light and dark cycle at 25±1° C. Animals are given standard laboratory chow (NIN, Hyderabad, India) and water, ad libitum. SAM of 20–25 g body weight range and Guinea pigs of 500–700 g body weight range are used (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107–114).

The test compounds will be administered orally to Swiss albino mice at 0.3 to 30 mg/kg/day dose for 6 days. Control mice will be treated with vehicle (0.25% Carboxymethylcellulose; dose 10 ml/kg). The test compounds will be administered orally to Guinea pigs at 0.3 to 30 mg/kg/day dose for 6 days. Control animals will be treated with vehicle (0.25% Carboxymethylcellulose; dose 5 ml/kg).

The blood samples will be collected in fed state 1 hour after drug administration on 0 and 6 day of treatment. The blood will be collected from the retro-orbital sinus through heparinised capillary in EDTA containing tubes. After centrifugation, plasma sample will be separated for triglyceride and total cholesterol (Wieland, O. Methods of Enzymatic analysis. Bergermeyer, H. O., Ed., 1963. 211–214; Trinder, P. Ann. Clin. Biochem. 1969. 6: 24–27). Measurement of plasma triglyceride, total cholesterol and HDL will be done using commercial kits (Dr. Reddy's Diagnostic Division, Hyderabad, India).

d) Body Weight Reducing Effect in Cholesterol Fed Hamsters

Male Syrian Hamsters are procured from NIN, Hyderabad, India. Animals are housed at DRF animal house under 12 hour light and dark cycle at 25±1° C. with free access to food and water. Animals are maintained with 1% cholesterol containing standard laboratory chow (NIN) from the day of treatment. The test compounds can be administered orally at 1 to 30 mg/kg/day dose for 15 days. Control group animals are treated with vehicle (Mill Q water, dose 10 ml/kg/day). Body weights are measured on every $3^{rd}$ day.

Formulae for Calculation:

1. Percent reduction in Blood sugar/triglycerides/total cholesterol were calculated according to the formula:

$$\text{Percent reduction } (\%) = \left[1 - \frac{TT/OT}{TC/OC}\right] \times 100$$

OC=Zero day control group value
OT=Zero day treated group value
TC=Test day control group value
TT=Test day treated group value 2. LDL and VLDL cholesterol levels were calculated according to the formula:

$$LDL \text{ cholesterol in mg/dl} = \left[\text{Total cholesterol} - HDL \text{ cholesterol} - \frac{\text{Triglyceride}}{5}\right] \text{mg/dl}$$

VLDL cholesterol in mg/dl=[Total cholesterol−HDL cholesterol−LDL cholesterol]mg/dl.

What is claimed is:

1. A pharmaceutically acceptable salt of the formula (I)

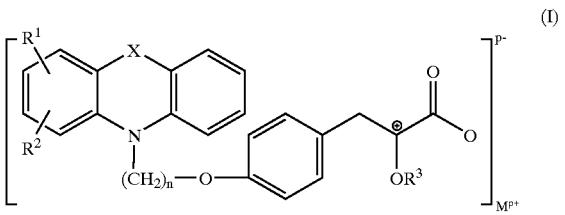

its tautomeric forms, its stereoisomers, its polymorphs, or is solvates wherein $R^1$ and $R^2$ are the same or different and independently represent hydrogen, halogen atom, hydroxy, nitro, cyano or lower alkyl group; X represents a heteroatom selected from oxygen or sulfur; $R^3$ represents hydrogen or lower alkyl group; n is an integer ranging from 1–4; M represents a counter ion or a moiety which forms a pharmaceutically acceptable salt; wherein M is selected from glucamine, -methyl glucamine, N-octyl glucamine, dicyclohexylamine, phenyl ethylamine, tris(hydroxymethyl) amino methane (tromethamine), phenylalaninol, mefformin, aminoguanidine, aminoguanidine hydrogen carbonate imidazole, piperazine, dimethyl piperazine, pyrrolidine, benzylamine, phenyl glycine methyl ester, phenylalanine benzyl ester, t-butyl amine or morpholine; and p is an integer ranging from 1 to 2.

2. A pharmaceutically acceptable salt which is selected from the group consisting of:

(±) 3-[4-[2-(Phenoxazin-10-yl)ethoxy]phenyl]-2-ethoxypropanoic acid imidazole salt;

(+) 3-[4-[2-(Phenoxazin-10-yl)ethoxy]phenyl]-2-ethoxypropanoic acid imidazole salt;

(−) 3-[4-[2-(Phenoxazin-10-yl)ethoxy]phenyl]-2-ethoxypropanoic acid imidazole salt;

(±) Di 3-[4-[2-(Phenoxazin-10-yl)ethoxy]phenyl]-2-ethoxypropanoic acid Piperazine salt;

(+) Di 3-[4-[2-(Phenoxazin-10-yl)ethoxy]phenyl]-2-ethoxypropanoic acid Piperazine salt;

(−) Di 3-[4-[2-(Phenoxazin-10-yl)ethoxy]phenyl]-2-ethoxypropanoic acid Piperazine salt;

(±) 3-[4-[2-(Phenoxazin-10-yl)ethoxy]phenyl]-2-ethoxypropanoic acid metformin salt;

(+) 3-[4-[2-(Phenoxazin-10-yl)ethoxy]phenyl]-2-ethoxypropanoic acid metformin salt;

(−) 3-[4-[2-(Phenoxazin-10-yl)ethoxy]phenyl]-2-ethoxypropanoic acid metformin salt;

(±) 3-[4-[2-(Phenoxazin-10-yl)ethoxy]phenyl]-2-ethoxypropanoic acid dimethylpiperazine salt;

(+) 3-[4-[2-(Phenoxazin-10-yl)ethoxy]phenyl]-2-ethoxypropanoic acid dimethylpiperazine salt;

(−) 3-[4-[2-(Phenoxazin-10-yl)ethoxy]phenyl]-2-ethoxypropanoic acid dimethylpiperazine salt;

(±) 3-[4-[2-(Phenoxazin-10-yl)ethoxy]phenyl]-2-ethoxypropanoic acid pyrrolidine salt;

(+) 3-[4-[2-(Phenoxazin-10-yl)ethoxy]phenyl]-2-ethoxypropanoic acid pyrrolidine salt;

(−) 3-[4-[2-(Phenoxazin-10-yl) ethoxy]phenyl]-2-ethoxypropanoic acid pyrrolidine salt;

(±) 3-[4-[2-(Phenoxazin-10-yl)ethoxy]phenyl]-2-ethoxypropanoic acid benzylamine salt;

(+) 3-[4-[2-(Phenoxazin-10-yl)ethoxy]phenyl]-2-ethoxypropanoic acid benzylamine salt;

(−) 3-[4-[2-(Phenoxazin-10-yl)ethoxy]phenyl]-2-ethoxypropanoic acid benzylamine salt;

(±) 3-[4-[2-(Phenoxazin-10-yl)ethoxy]phenyl]-2-ethoxypropanoic acid 1-phenyl ethyl amine salt;

(+) 3-[4-[2-(Phenoxazin-10-yl)ethoxy]phenyl]-2-ethoxypropanoic acid 1-phenyl ethyl amine salt;

(−) 3-[4-[2-(Phenoxazin-10-yl)ethoxy]phenyl]-2-ethoxypropanoic acid 1-phenyl ethyl amine salt;

(±) 3-[4-[2-(Phenoxazin-10-yl)ethoxy]phenyl]-2-ethoxypropanoic acid phenyl glycine methyl ester salt;

(+) 3-[4-[2-(Phenoxazin-10-yl)ethoxy]phenyl]-2-ethoxypropanoic acid phenyl glycine methyl ester salt;

(−) 3-[4-[2-(Phenoxazin-10-yl)ethoxy]phenyl]-2-ethoxypropanoic acid phenyl glycine methyl ester salt;

(±) 3-[4-[2-(Phenoxazin-10-yl)ethoxy]phenyl]-2-ethoxypropanoic acid phenylalanine benzyl ester salt;

(+) 3-[4-[2-(Phenoxazin-10-yl)ethoxy]phenyl]-2-ethoxypropanoic acid phenylalanine benzyl ester salt;

(−) 3-[4-[2-(Phenoxazin-10-yl)ethoxy]phenyl]-2-ethoxypropanoic acid phenylalanine benzyl ester salt;

(±) 3-[4-[2-(Phenoxazin-10-yl)ethoxy]phenyl]-2-ethoxypropanoic acid morpholine salt;

(+) 3-[4-[2-(Phenoxazin-10-yl)ethoxy]phenyl]-2-ethoxypropanoic acid morpholine salt;

(−) 3-[4-[2-(Phenoxazin-10-yl)ethoxy]phenyl]-2-ethoxypropanoic acid morpholine salt;

(±) 3-[4-[2-(Phenothiazin-10-yl)ethoxy]phenyl]-2-ethoxypropanoic acid metformin salt;

(+) 3-[4-[2-(Phenothiazin-10-yl)ethoxy]phenyl]-2-ethoxypropanoic acid metformin salt;

(−) 3-[4-[2-(Phenothiazin-10-yl) ethoxy]phenyl]-2-ethoxypropanoic acid metformin salt;

(±) 3-[4-[2-(Phenothiazin-10-yl)ethoxy]phenyl]-2-ethoxypropanoic acid phenylglycinol salt;

(+) 3-[4-[2-(Phenothiazin-10-yl)ethoxy]phenyl]-2-ethoxypropanoic acid phenylglycinol salt;

(−) 3-[4-[2-(Phenothiazin-10-yl) ethoxy]phenyl]-2-ethoxypropanoic acid phenylglycinol salt;

(±) 3-[4-[2-(Phenothiazin-10-yl)ethoxy]phenyl]-2-ethoxypropanoic acid 1-phenylalaninol salt;

(+) 3-[4-[2-(Phenothiazin-10-yl)ethoxy]phenyl]-2-ethoxypropanoic acid 1-phenylalaninol salt;

(−) 3-[4-[2-(Phenothiazin-10-yl)ethoxy]phenyl]-2-ethoxypropanoic acid 1-phenylalaninol salt;

(±) 3-[4-[2-(Phenothiazin-10-yl)ethoxy]phenyl]-2-ethoxypropanoic acid 1-phenyl ethylamine salt;

(+) 3-[4-[2-(Phenothiazin-10-yl)ethoxy]phenyl]-2-ethoxypropanoic acid 1-phenyl ethylamine salt;

(−) 3-[4-[2-(Phenothiazin-10-yl)ethoxy]phenyl]-2-ethoxypropanoic acid 1-phenyl ethylamine salt;

(±) 3-[4-[2-(Phenothiazin-10-yl)ethoxy]phenyl]-2-ethoxypropanoic acid imidazole salt;

(+) 3-[4-[2-(Phenothiazin-10-yl)ethoxy]phenyl]-2-ethoxypropanoic acid imidazole salt;

(−) 3-[4-[2-(Phenothiazin-10-yl)ethoxy]phenyl]-2-ethoxypropanoic acid imidazole salt;

Di (±) 3-[4-[2-(phenothiazin-10-yl)ethoxy]phenyl]-2-ethoxypropanoic acid piperazine salt;

Di (+) 3-[4-[2-(phenothiazin-10-yl)ethoxy]phenyl]-2-ethoxypropanoic acid piperazine salt;

Di (−) 3-[4-[2-(phenothiazin-10-yl)ethoxy]phenyl]-2-ethoxypropanoic acid piperazine salt;

(±) 3-[4-[2-(Phenothiazin-10-yl)ethoxy]phenyl]-2-ethoxypropanoic acid dimethyl piperazine salt;

(+)3-[4-[2-(Phenothiazin-10-yl)ethoxy]phenyl]-2-ethoxypropanoic acid dimethyl piperazine salt;

(−) 3-[4-[2-(Phenothiazin-10-yl)ethoxy]phenyl]-2-ethoxypropanoic acid dimethyl piperazine salt;

(±) 3-[4-[2-(Phenothiazin-10-yl)ethoxy]phenyl]-2-ethoxypropanoic acid benzylamine salt;

(+) 3-[4-[2-(Phenothiazin-10-yl)ethoxy]phenyl]-2-ethoxypropanoic acid benzylamine salt;

(−) 3-[4-[2-(Phenothiazin-10-yl)ethoxy]phenyl]-2-ethoxypropanoic acid benzylamine salt;

(±) 3-[4-[2-(Phenoxazin-10-yl)ethoxy]phenyl]-2-ethoxypropanoic acid dicyclohexylamine amine salt;

(+) 3-[4-[2-(Phenoxazin-10-yl)ethoxy]phenyl]-2-ethoxypropanoic acid dicyclohexylamine amine salt;

(−) 3-[4-[2-(Phenoxazin-10-yl)ethoxy]phenyl]-2-ethoxypropanoic acid dicyclohexylamine amine salt;

(±) 3-[4-[2-(Phenothiazin-10-yl)ethoxy]phenyl]-2-ethoxypropanoic acid dicyclohexylamine amine salt;

(+) 3-[4-[2-(Phenothiazin-10-yl)ethoxy]phenyl]-2-ethoxypropanoic acid dicyclohexylamine amine salt;

(−) 3-[4-[2-(Phenothiazin-10-yl) ethoxy]phenyl]-2-ethoxypropanoic acid dicyclohexylamine amine salt;

(±) 3-[4-[2-(Phenoxazin-10-yl)ethoxy]phenyl]-2-ethoxypropanoic acid amino guanidine salt;

(+) 3-[4-[2-(Phenoxazin-10-yl) ethoxy]phenyl]-2-ethoxypropanoic acid amino guanidine salt;

(−) 3-[4-[2-(Phenoxazin-10-yl)ethoxy]phenyl]-2-ethoxypropanoic acid amino guanidine salt;

(±) 3-[4-[2-(Phethioxazin-10-yl)ethoxy]phenyl]-2-ethoxypropanoic acid amino guanidine salt;

(+) 3-[4-[2-(Phenothiazin-10-yl)ethoxy]phenyl]-2-ethoxypropanoic acid amino guanidine salt, (−) 3-[4-[2-(Phenothiazin-10-yl)ethoxy]phenyl]-2-ethoxypropanoic acid amino guanidine salt;

(±) 3-[4-[2-(Phenoxazin-10-yl)ethoxy]phenyl]-2-ethoxypropanoic acid t-butyl amine salt;

(+) 3-[4-[2-(Phenoxazin-10-yl)ethoxy]phenyl]-2-ethoxypropanoic acid t-butyl amine salt;

(−) 3-[4-[2-(Phenoxazin-10-yl)ethoxy]phenyl]-2-ethoxypropanoic acid t-butyl amine salt;

(±) 3-[4-[2-(Phenoxazin-10-yl)ethoxy]phenyl]-2-ethoxypropanoic acid t-butyl amine salt;

(+) 3-[4-[2-(Phenothiazin-10-yl)ethoxy]phenyl]-2-ethoxypropanoic acid t-butyl amine salt and (−) 3-[4-[2-(Phenothiazin-10-yl)ethoxy]phenyl]-2-ethoxypropanoic acid t-butyl amine salt.

3. A pharmaceutical composition, which comprises a compound of formula (I)

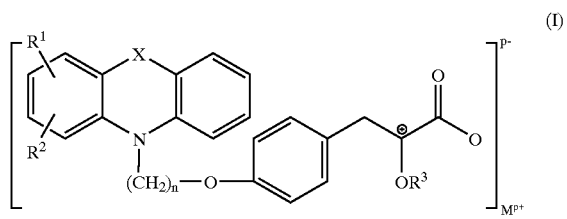

as defined in claim 1 and a pharmaceutically acceptable carrier, diluent, excipient or solvate.

4. A pharmaceutical composition, which comprises a compound as claimed in claim 1 and a pharmaceutically acceptable carrier, diluent, excipient or solvate.

5. A pharmaceutical composition which comprises a compound of formula (I) as defined in claim 1, and an HMG CoA reductase inhibitor, fibrate, nicotinic acid, cholestyramine, cholestipol, probucol or a mixture thereof and a pharmaceutically acceptable carrier, diluent, excipient or solvate.

6. A pharmaceutical composition which comprises a compound as claimed in claim 2, and an HMG CoA reductase inhibitor, fibrate, nicotinic acid, cholestyramine, cholestipol, probucol or a mixture thereof and a pharmaceutically acceptable carrier, diluent, excipient or solvate.

7. A pharmaceutical composition as claimed in claim 3, in the form of a tablet, capsule, powder, syrup, solution or suspension.

8. A pharmaceutical composition as claimed in claim 4, in the form of a tablet, capsule, powder, syrup, solution or suspension.

9. A pharmaceutical composition as claimed in claim 5, in the form of a tablet, capsule, powder, syrup, solution or suspension.

10. A pharmaceutical composition as claimed in claim 6, in the form of a tablet, capsule, powder, syrup, solution or suspension.

11. A method of treating hyperlipidemia, hypercholesteremia, hyperglycemia, insulin resistance or type II diabetes in which insulin resistance is an underlying pathophysiological mechanism comprising administering a compound of formula (I) as defined in claim 1 to a patient in need thereof.

12. A method of treating hyperlipidemia, hypercholesteremia, hyperglycemia, insulin resistance or type II diabetes in which insulin resistance is an underlying pathophysiological mechanism comprising administering a compound of formula (I) as defined in claim 2 to a patient in need thereof.

13. A method of treating hyperlipidemia, hypercholesteremia, hyperglycemia, insulin resistance or type II diabetes in which insulin resistance is an underlying pathophysiological mechanism comprising administering a compound of formula (I) as defined in claim 3 to a patient in need thereof.

14. A method of treating hyperlipidemia, hypercholesteremia, hyperglycemia, insulin resistance or type II diabetes in which insulin resistance is an underlying pathophysiological mechanism comprising administering a compound of formula (I) as defined in claim 4 to a patient in need thereof.

15. A method of treating hyperlipidemia, hypercholesteremia, hyperglycemia, insulin resistance or type (II) diabetes in which insulin resistance is an underlying pathophysiological mechanism comprising administering a compound of formula (I) as defined in claim 5 to a patient in need thereof.

16. A method of treating hyperlipidemia, hypercholesteremia, hyperglycemia, insulin resistance or type (II) diabetes in which insulin resistance is an underlying pathophysiological mechanism comprising administering a compound of formula (I) as defined in claim 6.

17. A method of reducing total cholesterol, blood plasma glucose, triglycerides, LDL, VLDL or free fatty acids or increasing HDL in the plasma comprising administering a compound of formula (I), as defined in claim 1 to a patient in need thereof.

18. A method of reducing total cholesterol, blood plasma glucose, triglycerides, LDL, VLDL or free fatty acids or increasing HDL in the plasma comprising administering a compound as claimed in claim 2 to a patient in need thereof.

19. A method of reducing total cholesterol, blood plasma glucose, triglycerides, LDL, VLDL or free fatty acids or increasing HDL in the plasma comprising administering a pharmaceutical composition according to claim 3 to a patient in need thereof.

20. A method of reducing total cholesterol, blood plasma glucose, triglycerides, LDL, VLDL or free fatty acids or increasing HDL in the plasma comprising administering a pharmaceutical composition according to claim 4 to a patient in need thereof.

21. A method of reducing total cholesterol, blood plasma glucose, triglycerides, LDL, VLDL or free fatty acids or increasing HDL in the plasma comprising administering a pharmaceutical composition according to claim 5 to a patient in need thereof.

22. A method of reducing total cholesterol, blood plasma glucose, triglycerides, LDL, VLDL or free fatty acids or increasing HDL in the plasma comprising administering a pharmaceutical composition according to claim 6 to a patient in need thereof.

23. A method of treating hyperlipemia, hypercholesteremia, hyperglycemia, insulin resistance, or type (II) diabetes in which insulin resistance is the underlying pathophysiological mechanism comprising administering to a patient in need thereof an effective amount of a compound as claimed in claim 1 in combination/concomittant with a HMG CoA reductase inhibitor, fibrate, nicotinic acid, cholestyramine, colestipol or probucol or a mixture thereof within such a period so as to act synergistically.

24. A method of treating hyperlipemia, hypercholesteremia, hyperglycemia, insulin resistance, or type (II) diabetes in which insulin resistance is the underlying pathophysiological mechanism comprising administering to a patient in need thereof an effective amount of a compound as claimed in claim 2 in combination/concomittant with a HMG CoA reductase inhibitor, fibrate, nicotinic acid, cholestyramine, colestipol or probucol or a mixture thereof within such a period so as to act synergistically.

25. A method of treating hyperlipemia, hypercholesteremia, hyperglycemia, insulin resistance, or type (II) diabetes in which insulin resistance is the underlying pathophysiological mechanism comprising administering to a patient in need thereof an effective amount of a compound as claimed in claim 3 in combination/concomittant with a HMG CoA reductase inhibitor, fibrate, nicotinic acid, cholestyramine, colestipol or probucol or a mixture thereof within such a period so as to act synergistically.

26. A method of treating hyperlipemia, hypercholesteremia, hyperglycemia, insulin resistance, or type (II) diabetes in which insulin resistance is the underlying pathophysiological mechanism comprising administering to a patient in need thereof an effective amount of a compound as claimed in claim 4 in combination/concomittant with a HMG CoA reductase inhibitor, fibrate, nicotinic acid, cholestyramine, colestipol or probucol or a mixture thereof within such a period so as to act synergistically.

27. A method of reducing plasma glucose, triglycerides, total cholesterol, LDL, VLDL or free fatty acids or increasing HDL in the plasma, which comprises administering a compound of formula (I) claimed in claim 1 in combination/concomittant with a HMG CoA reductase inhibitor, fibrate, nicotinic acid, cholestyramine, colestipol or probucol or a mixture thereof which may be administered together or within such a period as to act synergistically together to a patient in need thereof.

28. A method of reducing plasma glucose, triglycerides, total cholesterol, LDL, VLDL or free fatty acids or increasing HDL in the plasma, which comprises administering a compound as claimed in claim 2 in combination/concomittant with a HMG CoA reductase inhibitor, fibrate, nicotinic acid, cholestyramine, colestipol or probucol or a mixture thereof which may be administered together or within such a period as to act synergistically together to a patient in need thereof.

29. A method of reducing plasma glucose, triglycerides, total cholesterol, LDL, VLDL or free fatty acids or increasing HDL in the plasma, which comprises administering a pharmaceutical composition according to claim 3, in combination/concomittant with a HMG CoA reductase inhibitor, fibrate, nicotinic acid, cholestyramine, colestipol or probucol or a mixture thereof which may be administered together or within such a period as to act synergistically together to a patient in need thereof.

30. A method of reducing plasma glucose, triglycerides, total cholesterol, LDL, VLDL or free fatty acids or increasing HDL in the plasma, which comprises administering a pharmaceutical composition according to claim 4, in combination/concomittant with a HMG CoA reductase inhibitor, fibrate, nicotinic acid, cholestyramine, colestipol or probucol or a mixture thereof which may be administered together or within such a period as to act synergistically together to a patient in need thereof.

31. A process for the preparation of a pharmaceutically acceptable salt of the formula (I), its tautomeric forms, or its stereoisomers

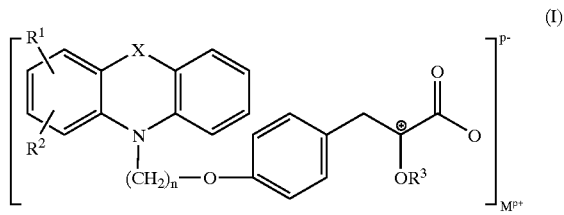

which comprises: reacting a compound of the formula (III)

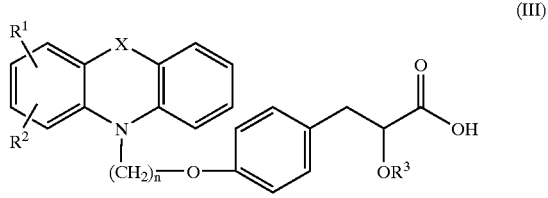

wherein $R^1$ and $R^2$ are the same or different and independently represent hydrogen, halogen atom, hydroxy, nitro, cyano or lower alkyl group; X represents a heteroatom selected from oxygen or sulfur; $R^3$ represents hydrogen or lower alkyl group; n is an integer ranging from 1–4; and p is an integer ranging from 1 to 2 with a stoichiometric amount of a base in the presence of a solvent wherein the base used is selected from lithium hydroxide, glucamine, -methyl glucamine, N-octyl glucamine, dicyclohexylamine, phenyl ethylamine, tris(hydroxymethyl)amino pethane (tromethamine), phenylalaninol, metformin, aminoguanidine, aminoguanidine hydrogen carbonate, imidazole, piperazine, dimethyl piperazine, pyrrolidine, benzylamine, phenyl glycine methyl ester, phenylalanine benzyl ester, t-butyl amine or morpholine.

32. The process as claimed in claim 31, wherein the reaction is effected in the presence of solvent selected from alcohols, ketones, ethers, DMF, DMSO, xylene, toluene, ethyl acetate or a mixture thereof.

33. The process as claimed in claim 31, wherein the reaction is carried out at a temperature in the range of −10° C. to the boiling point of the solvent employed for a period in the range of 10 minutes to 30 hours.

34. The process as claimed in claim 32, wherein the reaction is carried out at a temperature in the range of −10° C. to the boiling point of the solvent employed for a period in the range of 10 minutes to 30 hours.

35. The process as claimed in claim 32, wherein the alcohol is selected from a group consisting of ethanol, methanol, isopropanol and butanol; ketone is selected from a group consisting of acetone, diethyl ketone, and methyl ethyl ketone; and ether is selected from a group consisting of diethyl ether, ether, tetrahydrofuran, dioxane, and dibutyl ether.

* * * * *